(12) United States Patent
Panescu

(10) Patent No.: US 6,735,465 B2
(45) Date of Patent: May 11, 2004

(54) SYSTEMS AND PROCESSES FOR REFINING A REGISTERED MAP OF A BODY CAVITY

(75) Inventor: Dorin Panescu, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 288 days.

(21) Appl. No.: 10/145,125

(22) Filed: Oct. 24, 2001

(65) Prior Publication Data

US 2003/0078509 A1 Apr. 24, 2003

(51) Int. Cl.[7] .............................. A61B 5/05; A61B 5/04
(52) U.S. Cl. ...................................... 600/509; 600/508
(58) Field of Search .............................. 607/122, 116, 607/119; 600/508, 509

(56) References Cited

U.S. PATENT DOCUMENTS

| | | |
|---|---|---|
| 4,697,595 A | 10/1987 | Breyer et al. |
| 4,706,681 A | 11/1987 | Breyer et al. |
| 4,951,677 A | 8/1990 | Crowley et al. |
| 5,000,185 A | 3/1991 | Yock |
| 5,115,814 A | 5/1992 | Griffith et al. |
| 5,236,424 A | 8/1993 | Imran |
| 5,254,088 A | 10/1993 | Lundquist et al. |
| 5,281,218 A | 1/1994 | Imran |
| 5,314,408 A | 5/1994 | Salmon et al. |
| 5,383,874 A | 1/1995 | Jackson et al. |
| 5,385,148 A | 1/1995 | Lesh et al. |
| 5,391,199 A | 2/1995 | Ben-Haim |
| 5,409,000 A | 4/1995 | Imran |
| 5,421,338 A | 6/1995 | Crowley et al. |
| 5,443,489 A | 8/1995 | Ben-Haim |
| 5,464,016 A | 11/1995 | Nicholas et al. |
| 5,480,422 A | 1/1996 | Ben-Haim |
| 5,485,849 A | 1/1996 | Panescu et al. |
| 5,494,042 A | 2/1996 | Panescu et al. |
| 5,515,853 A | 5/1996 | Smith et al. |
| 5,546,951 A | 8/1996 | Ben-Haim |
| 5,558,091 A | 9/1996 | Acker et al. |
| 5,582,609 A | 12/1996 | Swanson et al. |
| 5,588,432 A * | 12/1996 | Crowley ..................... 607/122 |
| 5,595,183 A | 1/1997 | Swanson et al. |
| 5,636,634 A | 6/1997 | Kordis et al. |
| 5,647,870 A | 7/1997 | Kordis et al. |
| 5,662,108 A | 9/1997 | Budd et al. |
| 5,713,946 A | 2/1998 | Ben-Haim |
| 5,738,096 A | 4/1998 | Ben-Haim |
| 5,797,849 A | 8/1998 | Vesely et al. |
| 5,817,022 A | 10/1998 | Vesely |
| 5,833,621 A | 11/1998 | Panescu et al. |
| 5,941,251 A * | 8/1999 | Panescu et al. ............. 128/899 |
| 6,019,725 A | 2/2000 | Vesely et al. |
| 6,027,451 A | 2/2000 | McGee et al. |
| 6,070,094 A | 5/2000 | Swanson et al. |
| 6,095,150 A | 8/2000 | Panescu et al. |
| 6,101,409 A | 8/2000 | Swanson et al. |
| 6,216,027 B1 | 4/2001 | Willis et al. |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,491 B1 | 5/2001 | Kordis et al. |
| 6,292,681 B1 | 9/2001 | Moore |
| 6,314,310 B1 | 11/2001 | Ben-Haim et al. |
| 6,332,089 B1 | 12/2001 | Acker et al. |

* cited by examiner

Primary Examiner—Carl Layno
(74) Attorney, Agent, or Firm—Bingham McCutchen LLP

(57) ABSTRACT

A process of refining a map of a body cavity includes positioning a first probe and a second probe within the body cavity. Mapping elements on the first probe are used to gather local information from a plurality of locations along the body cavity. The absolute locations of the mapping elements are registered in a three-dimensional coordinate system, and are associated with the local information to generate the map. A mapping element on the second probe is then used to gather information local to a location between the plurality of locations along the body cavity. The absolute location of the mapping element is registered in the three-dimensional system and associated with the local information to refine the map.

40 Claims, 10 Drawing Sheets

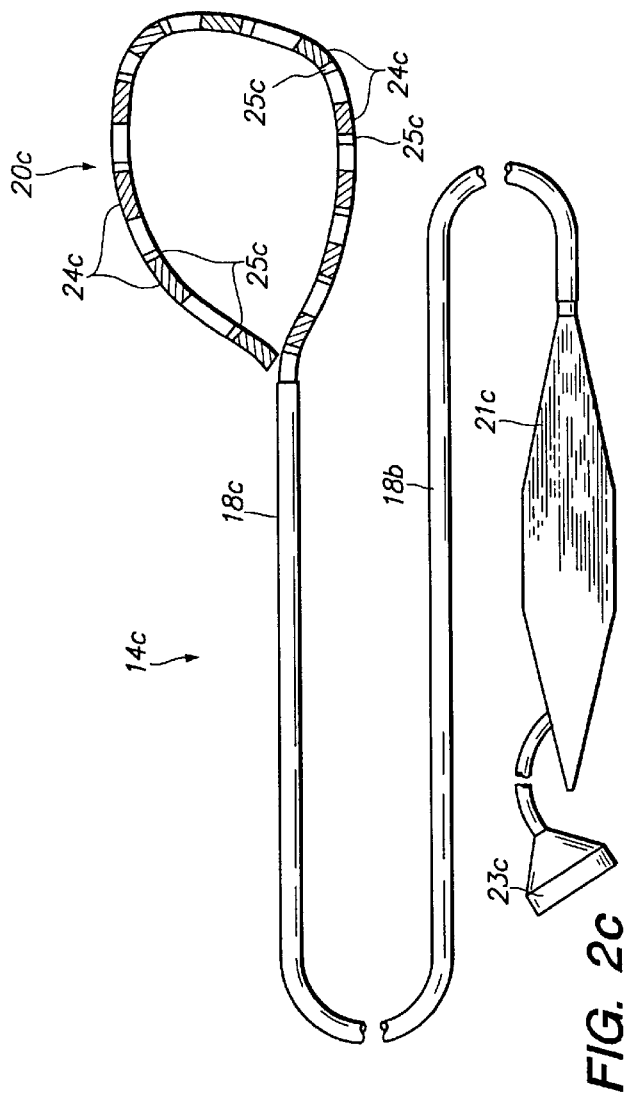
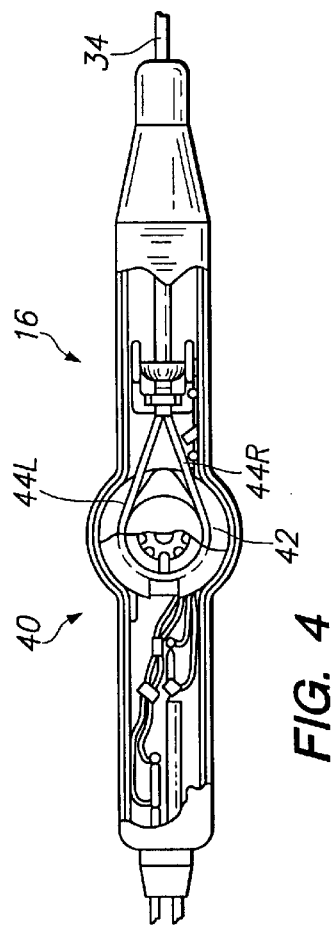
FIG. 2c
FIG. 4

SYSTEMS AND PROCESSES FOR REFINING A REGISTERED MAP OF A BODY CAVITY

FIELD OF THE INVENTION

The invention relates to systems and methods for guiding and locating diagnostic or therapeutic elements on medical instruments positioned in a body.

BACKGROUND OF THE INVENTION

The use of invasive medical devices, such as catheters and laparoscopes in order to gain access into interior regions or spaces of the body for performing diagnostic and therapeutic procedures is well known. In such procedures, it is important for a physician or technician to be able to precisely position the device, including various functional elements located on the device, within the body in order to make contact with a desired body tissue location.

For example, the need for precise control over the positioning of an invasive catheter or surgical probe is especially critical during procedures for testing or ablating myocardial tissue within the beating heart for treating cardiac rhythm disturbances. To perform such a procedure, the physician typically steers a catheter through a main vein or artery into the interior region of the heart that is to be treated. The physician then manipulates the catheter in order to place one or more electrodes carried on the distal portion and/or tip of the catheter into direct contact with the endocardial tissue. The physician may use the electrode(s) to examine the propagation of electrical impulses in heart tissue in order to locate aberrant conductive pathways and to identify the arrhythmia foci. This procedure is called mapping. One such mapping technique is to introduce multiple-electrode array structures carried on the distal end of an invasive catheter into the heart through venous or arterial access. Information obtained from the various electrode elements (operating in either unipolar or bipolar fashion), combined with externally obtained electrocardiogram signals, can be externally processed to detect local electrical events and identify likely arrhythmia foci locations within the heart.

Using the same, or a different catheter or surgical probe device, the physician may then direct energy from one or more distally carried electrode(s) through the myocardial tissue either to an indifferent electrode (in a unipolar electrode arrangement) or to an adjacent electrode (in a bipolar electrode arrangement) to ablate the tissue locations containing the aberrant conductive pathways in order to restore a healthy heart rhythm. This procedure is called ablation therapy.

In theory, minimally invasive mapping techniques allow a physician to identify a target ablation site within the heart, prior to the actual ablation procedure and without the complications of open heart surgery. In practice, however, current minimally invasive mapping techniques do not ensure that an identified target site will be accurately or easily relocated. Accordingly, it would be desirable to provide physicians with the ability to accurately return to a target site in the heart that was previously identified using minimally invasive mapping techniques.

One proposed solution to the problem of identifying and relocating target sites in the heart site is to add a navigation system that is centered outside of a patient's body, in order to provide an "absolute" reference frame that is unaffected by the absolute location of the patient. One such system, disclosed in U.S. Pat. No. 5,391,199 to Ben-Haim ("the '199 patent"), combines an electrophysiological mapping system and a navigational system centered on a reference frame outside of the body in order to attempt to increase a physician's ability to return to an identified target site. The mapping system provides data on points of interest at sites within the body. The exterior navigational system provides data on the "absolute" location of the site with respect to an external reference frame of the site as these points of interest are identified. This is accomplished by placing one or more location sensors adjacent mapping elements on the mapping probe. As taught in the '199 patent, combining the "location information" with "local information" for a sufficient number of sites will provide a three dimensional "map" of data points corresponding to the three-dimensional structure of the heart or other organ.

One problem, however, occurs with mapping catheters having relatively small mapping element carrying structures, e.g., 3-D catheter structures that are 40 mm in diameter or smaller. In these cases, it is difficult to place location elements adjacent all of the mapping elements, and sometimes even adjacent a select few of the mapping elements. Thus, generating a three dimensional map is made difficult. Another problem occurs as a result of the discrete nature of the mapping elements. Oftentimes, critical information is missed between the mapping elements, resulting in a map that, although corresponding to the three-dimensional structure of the heart or other organ, does not accurately identify target sites.

SUMMARY OF THE INVENTION

The present invention provides for systems and processes for refining a registered map.

In a first aspect of the present invention, a method of mapping a body cavity of a patient is provided. The body cavity may be, for example, a heart chamber. A first probe carrying a plurality of mapping elements is positioned adjacent a plurality of locations along the body cavity. The first probe may include a 3-D catheter structure on which the plurality of mapping elements is carried. In one embodiment, the 3-D catheter structure is 40 millimeters or less in size. A second probe carrying a functional element is also positioned in the body cavity. The absolute position, within a three-dimensional coordinate system, of the functional element is determined. Also, the proximity of that functional element to each of the plurality of mapping elements is determined. Based on the absolute position of the functional element and the proximity of the functional element to the mapping elements, an absolute position within the coordinate system of the mapping elements is determined. A map is generated by detecting information local to the body cavity, with the mapping elements, and associating the local information to the absolute positions of the mapping elements. The functional element is then located adjacent a location on the body cavity between the plurality of locations. Here, the functional element of the second probe comprises a mapping element. Prior to locating the functional element adjacent the body cavity location, in one alternative, the first probe is removed from the body cavity. In another alternative, the first probe is maintained within the body cavity while locating the functional element adjacent the body cavity location. The absolute position of the mapping element of the second probe, within the coordinate system, is determined. Additionally, information local to the body cavity is detected using the mapping element, and the local information is associated to the absolute position of the mapping element in order to refine the map.

In an alternative procedure of the first aspect of the present invention, a first probe carrying a plurality of mapping elements are located adjacent a plurality of locations along the body cavity. A second probe carrying a mapping element is positioned in the body cavity. An absolute position within a three-dimensional coordinate system is determined for each of the plurality of mapping elements. A map is generated by detecting local information using the plurality of mapping elements and associating that information to the absolute positions of the plurality of mapping elements. The mapping element of the second probe is adjacent a location on the body cavity between the plurality of locations. An absolute position of the mapping element is determined, local information is detected using the mapping element, and the local information is associated to the absolute position of the mapping element in order to refine the map.

For either of the above-mentioned procedures, the refined map is stored in memory, the refined map is retrieved from memory, and the refined map is displayed. A device is navigated within the coordinate system by reference to the displayed refined map. The navigated device may be the second probe. The navigated device may also be a therapeutic device used to treat targeted tissue identified by the local information. The therapeutic device may include an ablation element to ablate the targeted tissue.

In a second aspect of the present invention, a method of mapping a body cavity of a patient is provided. The method comprises positioning a mapping probe within the body cavity, generating a map of the body cavity with the mapping probe, and registering the map within a three-dimensional coordinate system. This can be accomplished using the previous map registration methods, or alternatively, using other map registration means. The method further comprises positioning a roving probe in the body cavity and refining the map with the roving probe.

The preferred method of refining the map may include locating the mapping element adjacent a location on the body cavity, determining an absolute position of the mapping element within the coordinate system, and detecting information local to the body cavity using the mapping element and associating the local information to the absolute position of the mapping element. Alternatively, other means of refining the map can be used. The preferred method may further include storing the refined map in memory, retrieving the refined map from memory, and displaying the refined map. A device can be navigated in the coordinate system by reference to the displayed refined map. The device can be a therapeutic device and the refined map can comprise information indicating tissue targeted for therapy, in which case, the method can further comprise treating the targeted tissue with the device, e.g., by ablating it with an ablation electrode. The mapping probe can be removed from the body cavity prior to refining the map, or alternatively, maintained within the body cavity while the map is refined. The body cavity can be a heart chamber or any other body cavity within the patient.

In a third aspect of the present invention, a system for mapping a body cavity is provided. The system includes a first probe having a distal portion carrying a plurality of mapping elements and one or more location elements, and a second probe having a distal portion carrying a mapping element and a location element. In one embodiment, the first probe includes a 3-D catheter structure to carry the plurality of mapping elements. In an embodiment of this first probe, the 3-D catheter structure is 40 millimeters or less in size. A mapping processing subsystem is provided that is in communication with the plurality of mapping elements and the mapping element. The mapping processing subsystem is configured for generating a map by detecting information local to the body cavity using the plurality of mapping elements and the mapping element. A location determination subsystem in communication with the one or more location elements and the location element determines absolute positions of the plurality of mapping elements and the mapping element in a three-dimensional coordinate system based on locations of the one or more location elements and the location element. A registration subsystem in communication with the mapping processing subsystem and the location determination subsystem associates the local information to the absolute positions of the plurality of mapping elements and the mapping element. Memory in communication with the registration subsystem is used for storing the refined map, and a display is used for displaying the refined map. In an alternative embodiment, a device carrying another location element, wherein the location determination subsystem is further in communication with another location element and is configured to determine an absolute position of the another location element, is provided. This device may be the second probe. Also, this device may be a therapeutic device, and may include an ablation electrode, capable of treating tissue targeted for therapy that is identified by the local information.

Other and further aspects and features of the invention will become apparent from the following drawings and detailed description.

BRIEF DESCRIPTION OF THE DRAWINGS

FIG. 2c illustrates an embodiment of a mapping probe having a linear functional element carrying structure.

FIG. 4 illustrates a steering structure of the roving ablation probe shown in FIG. 3.

DETAILED DESCRIPTION OF PREFERRED EMBODIMENTS

Figure 1:
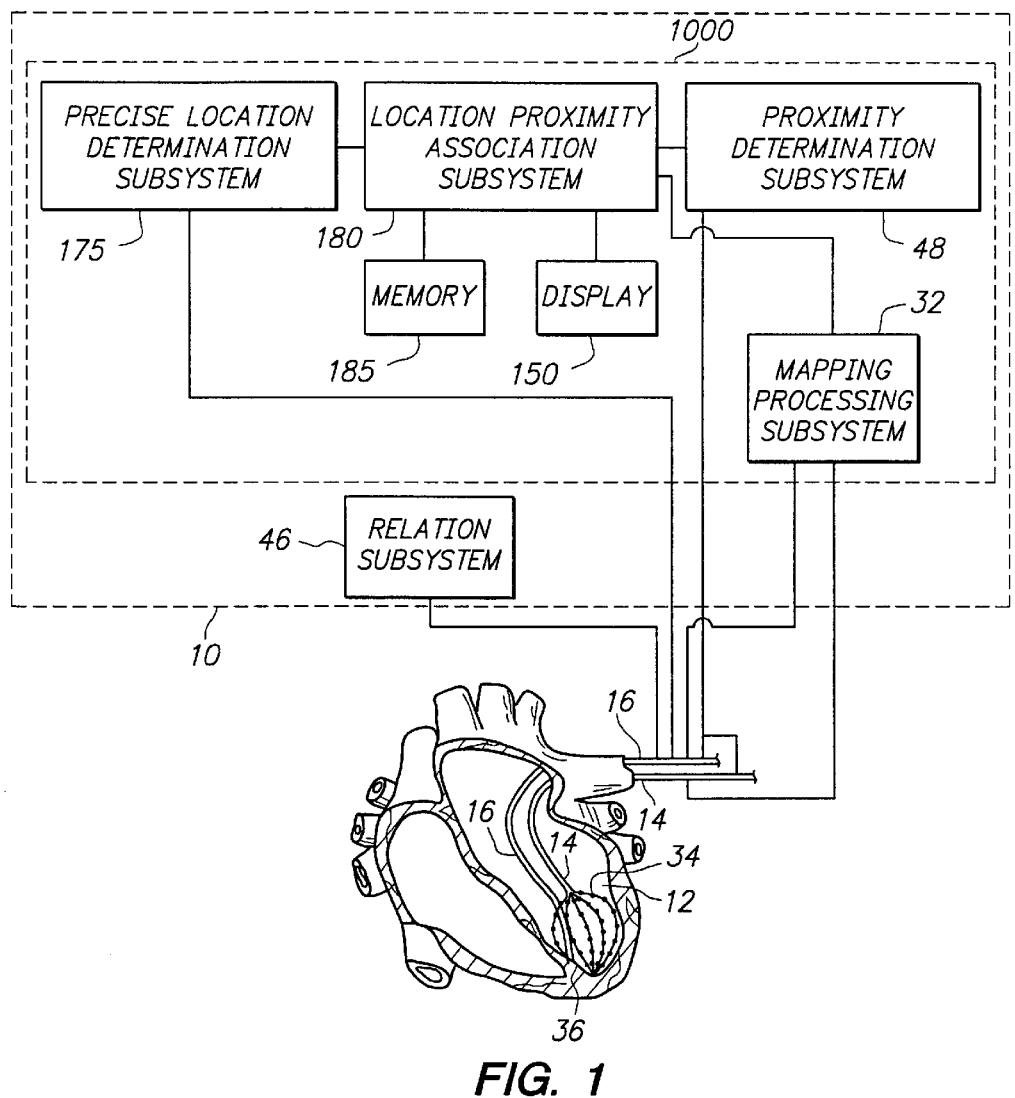
FIG. 1 illustrates an embodiment of a mapping probe and a roving ablation probe located within the heart of a patient.

FIG. 1 illustrates the components of a system 10 of the present invention for mapping a three-dimensional reference coordinate system, e.g., a volume or other three-dimensional space in a patient's body, and for accessing a targeted region in the three-dimensional coordinate system for performing diagnostic or therapeutic procedures. The embodiment illustrated in FIG. 1 shows the system 10 for mapping a three-dimensional coordinate system within a heart and for being used for ablating heart tissue, which is one use for which the invention is well suited. Nevertheless, it should be appreciated that the invention is applicable for use in other applications. For example, the various aspects of the invention have application in procedures for ablating tissue in the prostate, brain, gall bladder, uterus, esophagus and other regions of the body. Additionally, it should be appreciated that the invention is applicable for use in drug therapy applications where a therapeutic agent is delivered to a targeted tissue region. The system 10 includes deployable, invasive medical devices, such as catheters, surgical or laparoscopic probes, but is not limited to any particular type of invasive device. It is noted that the heart illustrated in FIG. 1 is not anatomically accurate, but is rather shown in diagrammatic form in order to demonstrate the features of the invention.

As illustrated, the system 10 includes a map registration system 1000 and ablation system 46 coupled to a mapping probe 14 and a roving ablation probe 16 deployed and ready for use within a selected region 12, and specifically within the left ventricle of the heart. The probes of the system 10 may, of course, also be deployed in other regions of the heart or the body. As will be described in further detail below, the mapping probe 14 is used to find and map targeted ablation sites, and the roving probe 16 is used to treat the targeted ablation sites. It should be noted, however, that the present inventions should not be limited to the use of a mapping probe 14 or ablation probe 16, but rather any suitable device that can be placed within the selected region can be used. For example, instead of an ablation probe, a probe that includes an element suitable for delivering a therapeutic agent can be used. Further embodiments of suitable probes will be subsequently illustrated and described. It is further noted that although the mapping probe 14 and ablation probe 16 are illustrated as separate devices, they can also be embodied in an integrated device. Moreover, a plurality of mapping probes 14 may used, rather than the single mapping probe 14 shown in FIG. 1.

Further details for the deployment and structures of the devices 14 and 16 are described in U.S. Pat. No. 5,636,634, entitled "Systems and Methods Using Guide Sheaths for Introducing, Deploying, and Stabilizing Cardiac Mapping and Ablation Probes," the disclosure of which is incorporated by reference.

1. Mapping Subsystem

Figures 2A, 2B:
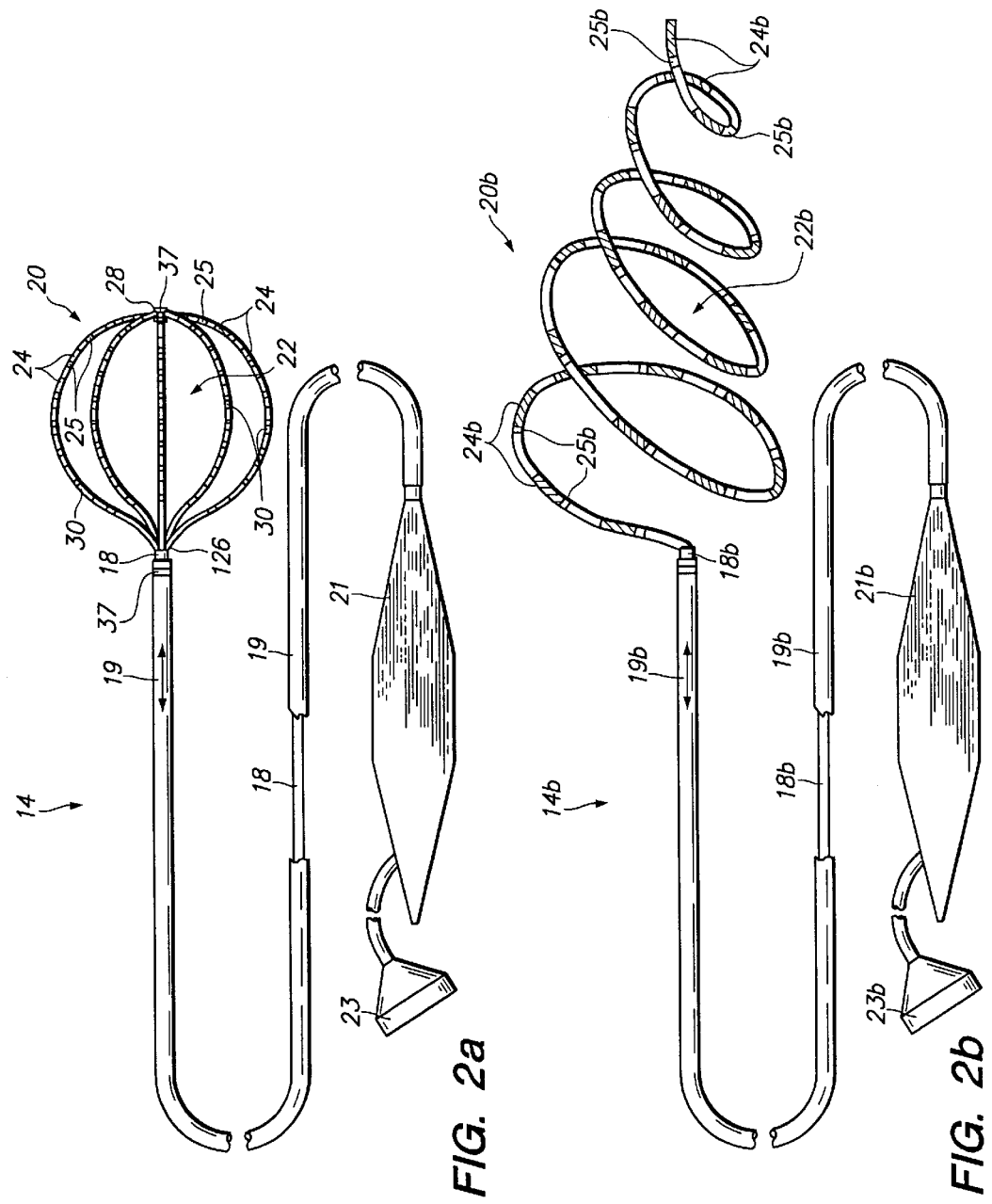
FIG. 2a shows an embodiment of a mapping probe having a basket functional element carrying structure suitable for use with the present invention.
FIG. 2b shows an embodiment of a mapping probe having a helically wound functional element carrying structure that may be used with the present invention.

Referring further to FIG. 2a, the mapping probe 14 has a flexible catheter body 18, the distal end of which carries a three dimensional structure 20 configured to carry a plurality of mapping elements 24. A proximity element 25 is preferably located adjacent each mapping element 24. Alternatively, the mapping elements 24 can be used as the proximity elements 25. As will be described in further detail below, the mapping elements 24 sense electrical activity in the heart tissue, which sensed activity is then processed by a mapping processing subsystem 32 to assist the physician in identifying the site or sites within the heart appropriate for ablation. This process is commonly referred to as mapping.

As illustrated, the structure 20 takes the form of a basket defining an open interior space 22. It is noted that other three dimensional structures could be deployed on the distal end, as will be described in further detail below. It is further noted that the multiple mapping elements 24 may be disposed on more than one structure rather than, for example, the single mapping probe 14 illustrated in FIG. 2a. For example, if mapping within a right atrium of a heart is desired, a probe arrangement comprising a decapolar catheter carrying multiple mapping elements for positioning in the coronary sinus, and a loop catheter carrying multiple mapping elements for positioning around the tricuspid annulus may be used. As another example, if mapping within a left atrium is desired, probe arrangement comprising a coronary sinus catheter carrying multiple mapping elements and a basket catheter carrying multiple mapping elements positioned in the left atrium may be used.

The illustrated 3-D catheter structure 20 comprises a base member 26 and an end cap 28 between which flexible splines 30 generally extend in a circumferentially spaced relationship. The splines 30 are preferably made of a resilient inert material, such as, e.g., Nitinol metal or silicone rubber, and are connected between the base member 26 and the end cap 28 in a resilient, pretensed condition, to bend and conform to the tissue surface they contact. In the illustrated embodiment, eight splines 30 form the 3-D catheter structure 20. Additional or fewer splines 30 could be used in other embodiments. As illustrated, each spline 30 carries eight mapping elements 24. Additional or fewer mapping elements 24 could be disposed on each spline 30 in other embodiments of the 3-D catheter structure 20. In the illustrated embodiment, the 3-D catheter structure 20 is preferably relatively small, such as, e.g., 40 mm or less in diameter. This is not to say, however, that the present inventions cannot be applied to larger 3-D catheter structures, such as, e.g., those that are 70 mm in diameter or greater.

A slidable sheath 19 is movable along the axis of the catheter body 18. Moving the sheath 19 forward causes the sheath 19 to move over the 3-D catheter structure 20, thereby collapsing the structure 20 into a compact, low profile condition suitable for introduction into an interior space, such as, e.g., into the heart region 12. In contrast, moving the sheath 19 rearward frees the 3-D catheter structure 20, allowing the structure 20 to spring open and assume the pretensed position illustrated in FIG. 2a. Further details of the 3-D catheter structure are disclosed in U.S. Pat. No. 5,647,870, entitled "Multiple Electrode Support Structures," the disclosure of which is expressly and fully incorporated by reference.

A signal wire (not shown) is electrically coupled to each mapping element 24. The wires extend through the body 18 of the mapping probe 14 into a handle 21, in which they are coupled to an external connector 23, which may be a multiple pin connector. The connector 23 electrically couples the mapping elements 24 to the mapping processing system 32. Further details on mapping systems are discussed in U.S. Pat. No. 6,070,094, entitled "Systems and Methods for Guiding Movable Electrode Elements within Multiple-Electrode Structure," and U.S. Pat. No. 6,233,491, entitled "Cardiac Mapping and Ablation Systems," the disclosures of which are expressly and fully incorporated herein by reference. In a similar manner, a signal wire electrically couples each proximity element 25 to the proximity determination subsystem 48.

Other embodiments of mapping catheters can be envisioned. For example, turning to FIG. 2b, an embodiment of a mapping probe 14b is shown wherein the mapping probe 14b includes a flexible catheter body 18b, the distal end of which carries a three dimensional, helically wound structure 20b carrying a plurality of mapping elements 24b and proximity elements 25b. Alternatively, the mapping elements 24b can be used as the proximity elements 25b. As illustrated, the structure 20b takes the form of a helix that defines an open interior space 22b. The structure 20b is preferably made of a resilient inert material, such as, e.g., Nitinol metal or silicone rubber. The mapping probe 14 further comprises a slidable sheath 19b movable along the axis of the catheter body 18b is provided, as shown by the arrows in FIG. 2b. As with the mapping probe 14 shown in FIG. 2a, moving the sheath 19b forward causes the sheath 19b to move over the helical structure 20b, thereby collapsing the structure 20b into a compact, low profile condition suitable for introduction into a three-dimensional coordinate system in a space, such as, e.g., into the heart region 12. Moving the sheath 19b rearward frees the helical structure 20b, allowing the structure 20b to spring open and assume the pretensed position shown in FIG. 2b.

The structure 20b carries an array of mapping elements 24b and proximity elements 25b adjacent each mapping element 24b. A signal wire (not shown) is electrically coupled to each mapping element 24b. The wires extend through the body 18b of the mapping probe 14b into a handle 21b, in which they are coupled to an external connector 24, which may be a multiple pin connector. The operation of the mapping elements 24b is substantially similar to the operation of the mapping elements 24 on mapping probe 14 illustrated in FIG. 2a and previously discussed. Also, a signal wire (not shown) electrically couples each proximity element 25b to the proximity determination subsystem 48.

Turning now to FIG. 2c, an embodiment of a mapping probe 14c is shown that includes a flexible catheter body 18c with a distal end that carries a two dimensional, linear functional element carrying structure 20c. As illustrated, the structure 20c is a linear structure that is capable of conforming to a tissue surface against which it is depressed. The structure 20c is preferably made of a resilient inert material, such as, e.g., Nitinol metal or silicone rubber.

The structure 20c carries an array of mapping elements 24c and proximity elements 25c. A signal wire (not shown) is electrically coupled to each mapping element 24c and proximity element 25c. Again, alternatively the mapping elements 24c can be used as the proximity elements 25c. The wires extend through the body 18c of the mapping probe 14c into a handle 21c, in which they are coupled to an external connector 23c, which may be a multiple pin connector. Also, a steering mechanism (not shown) may be provided on the handle 21c. In this embodiment, the steering mechanism facilitates placement of the carrying structure 20c against a surface. The operation of the steering mechanism is similar to the steering mechanism of one embodiment of the second probe, which will be discussed herein. As with the mapping elements 24b shown in FIG. 2b, the operation of the mapping elements 24c is substantially similar to the operation of the mapping elements 24 on mapping probe 14 illustrated in FIG. 2a and previously discussed. Also, each proximity element 25c is coupled to the proximity determination subsystem 48.

Although the mapping elements 24 have been described as being carried by mapping dedicated probes, such as mapping probes 14a–14c, mapping elements can be carried on non-mapping dedicated probes. For example, referring to FIG. 14, the roving probe 16 alternatively includes a mapping element 33 disposed on the distal end of the catheter body 34. The mapping element 33 of the roving probe 16 is coupled to the mapping processing system 32. Alternatively, rather than including a mapping element 33, the ablation element 36 of the roving probe 16 is coupled to the mapping processing system 32, and functions as a mapping electrode. These embodiments of the roving probe 16 enables the system 10 to refine a registered map using the roving probe 16, using a procedure that will be described in further detail herein.

2. Ablation System

Figure 3:
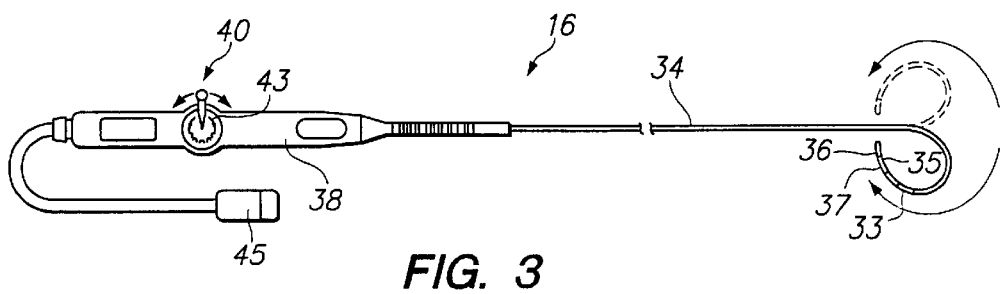
FIG. 3 illustrates a roving ablation probe suitable for use with the present invention.

Referring further to FIGS. 3 and 4, the roving probe 16 includes a flexible catheter body 34, the distal end of which carries a single ablation element 36 and a proximity element 35 adjacent the ablation element 36. Additionally, a location element 37 is adjacent either of the ablation 36 or proximity 35 elements. In the illustrated embodiment, the location element is shown adjacent the proximity element 35. Alternatively, the location element 37 and proximity element 35 can be combined into a single structural element, or even more alternatively, the ablation element 36, location elements 37, and proximity element 35 can be combined into a single structural element. Other configurations employing multiple functional elements are possible. U.S. Pat. No. 5,582,609, entitled "Systems and Methods for Forming Large Lesions in Body Tissue Using Curvilinear Electrode Elements," which is expressly and fully incorporated herein by reference, describes an embodiment using multiple ablation elements 36.

A handle 38 is attached to the proximal end of the catheter body 34. The handle 38 and the catheter body 34 carry a steering mechanism 40 for selectively bending or flexing the catheter body 34 along its length, as the arrows in FIG. 3 show. The steering mechanism 40 can vary. In the illustrated embodiment, the steering mechanism 40 includes a rotating cam wheel 42 with an external steering lever 43. The cam wheel 42 holds the proximal ends of right and left steering wires, designated 44R and 44L. The wires 44R and 44L pass through the catheter body 34 and connect to the left and right sides of a resilient bendable wire or spring (not shown) at the distal end of the body 34. Movement of the steerable lever flexes the distal end of the body 34 to bring the ablation element 36 into conforming, intimate contact against a target surface. Further details of the steering mechanism 40 are described in U.S. Pat. No. 5,254,088, entitled "Catheter Steering Mechanism," which is expressly and fully incorporated herein by reference.

A wire (not shown) electrically connected to the ablation element 36 extends through the catheter body 34 into the handle 38, where it is electrically coupled to an external connector 45, which connects the ablation element 36 to the ablation system 46.

In a similar manner, a wire (not shown) electrically connects the proximity element 35 to the proximity determination subsystem 48 and the location element 37 to the location determination subsystem 175. The ablation system 46 is preferably a radio frequency (RF) generator. Any suitable ablation system 46 may be utilized, however, including, e.g., a microwave generator, an ultrasound generator, a cryoablation generator, and a light energy or other optical energy generator. Details on the use and structure of an ablation system, particularly a RF system, suitable for use with the system 10 are disclosed in U.S. Pat. No. 5,383,874, entitled "Systems for Identifying Catheters and Monitoring Their Use," which is expressly and fully incorporated herein by reference.

A suitable ablation element 36 is utilized depending on the type of system 46 used. For example, a laser diode, light emitting diode, or fiber optic transmitting laser beam is used as ablation element 36 if a light energy or optical energy generator is used. A cryoablation element is used as ablation element 36 if a cryoablation energy generator is used. Similarly, a microwave transmitter is used as ablation element 36 if a microwave generator is utilized, an ultrasound transmitter is used as the ablation element 36 if an ultrasound generator is used, and an electrode is used as the ablation element 36 when a RF generator is utilized. Further details on ablation systems are discussed in U.S. Pat. No. 6,070,094, entitled "Systems and Methods for Guiding Movable Electrode Elements within Multiple-Electrode Structure," which is expressly and fully incorporated herein by reference.

3. Map Registration System

Figure 14:
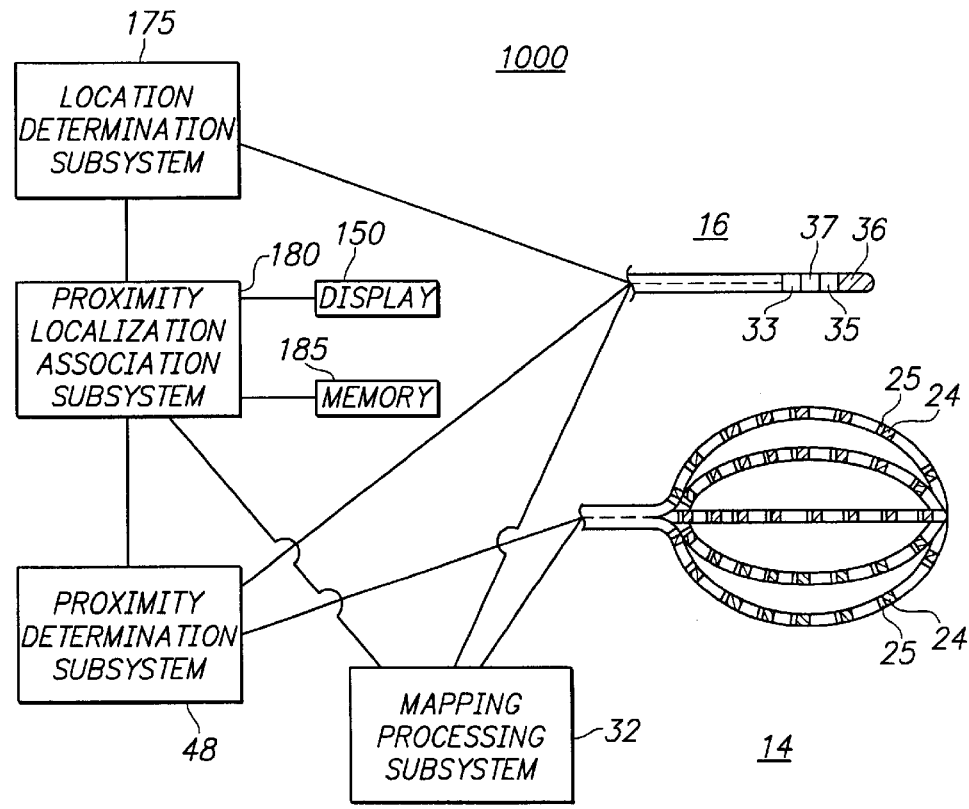
FIG. 14 illustrates one embodiment of a map registration system of the present invention that can be used with the mapping and roving probe of FIG. 1.

To aid in locating the targeted ablation sites, the map registration system 1000 is configured for registering the map generated by the mapping processing subsystem 32 in a three-dimensional coordinate system. To this end, the map registration system 1000, in addition to the mapping processing subsystem 32, comprises a proximity determination subsystem 48, a precise location determination subsystem 175, and a location-proximity association subsystem 180, as illustrated in FIG. 14. Briefly, the proximity determination subsystem 48 determines the proximity of a proximity element 35 (and thus a location element 37) mounted on the roving probe 16 relative to one or more proximity elements 25 (and thus, the mapping elements 24) located on the mapping probe 14; the precise location determination subsystem 175 locates the absolute position of the location element 37 in the three-dimensional coordinate system; and the location-proximity association subsystem 180 determines the absolute position of the proximity elements 25, and thus the mapping elements 24, in the three-dimensional coordinate system based on the proximity between the proximity element 35 and proximity elements 25 and the absolute position of the location element 37.

A. Proximity Determination Subsystem

As illustrated in FIG. 14, the proximity determination subsystem 48 is electrically coupled to the mapping probe 14 and the roving probe 16, and specifically a proximity element 35 located adjacent the ablation electrode 36 and proximity elements 25 located adjacent the mapping elements 24. Alternatively, rather than having distinct proximity elements 35, 25, the ablation electrode 36 or mapping elements 24 can act as proximity elements 35,25, depending on the implementation of the proximity determination subsystem 48, as will be discussed in further detail below. The proximity determination subsystem 48 collects and processes information regarding the proximity of proximity element 35 carried by the roving probe 16 to the proximity elements 25 carried by the mapping probe 14, and thus the proximity of the ablation electrode 36 to the mapping elements 24. The proximity determination subsystem 48 can process and provide position specific information in various ways. Representative modes of operation for the proximity determination subsystem 48 will now be described.

1) Ultrasound Time-Delay Mode

Figure 5:
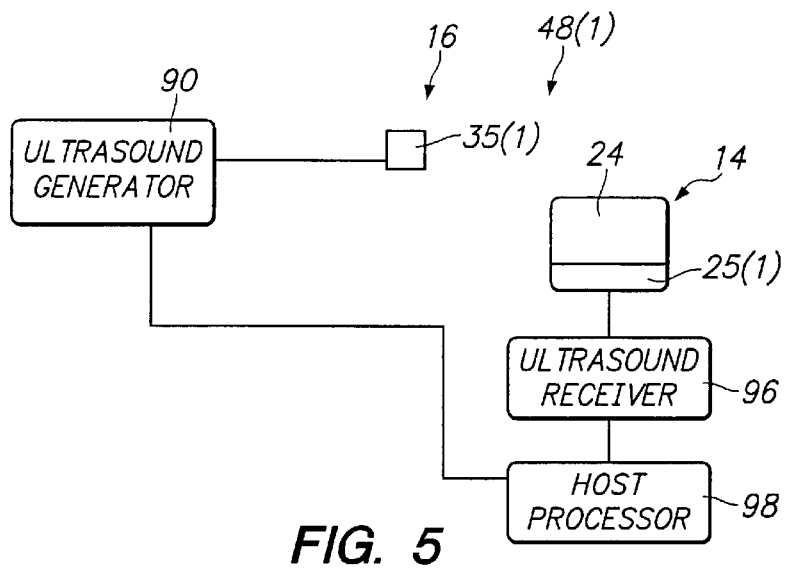
FIG. 5 illustrates an embodiment of the proximity determination subsystem that utilizes ultrasonic signals.

FIG. 5 shows one implementation of the proximity determination subsystem, designated 48(1). Here, the proximity elements 25(1), 35(1) are ultrasound transducers. The subsystem 48(1) analyzes delays in the transmission of ultrasonic signals between an ultrasound transducer proximity element 25(1) located adjacent each mapping element 24 and an ultrasound transducer proximity element 35(1) located on the roving probe 16. In one embodiment, the proximity element 35(1) is located adjacent or near the ablation element 36 or other treatment element of the roving probe 16. The proximity determination subsystem 48(1) generates an ultrasonic field between the proximity element 35(1) of the roving probe 16 and the proximity elements 25(1) near the mapping elements 24 of the mapping probe 14. The proximity determination subsystem 48(1) analyzes the ultrasonic information to locate the proximity of the proximity element 35(1) relative to the proximity elements 25(1). Alternatively, in embodiments where the mapping elements 24 incorporate the proximity elements, an ultrasonic field is generated between the proximity element 35(1) and the mapping elements 24.

The proximity determination subsystem 48(1) includes an ultrasound generator 90 coupled to the ultrasound transducer proximity element 35(1). The proximity element 35(1) can take the form of a phased array of piezoelectric crystals that produce a planar wave form, for example. Alternatively, the proximity element 35(1) may be a single piezoelectric crystal. Breyer et al., U.S. Pat. No. 4,706,681, discloses examples of the ultrasound transducers that can be used in association with the proximity determination subsystem 48(1). In another embodiment, the ablation element 36 is an ultrasound transducer, incorporating the function of the proximity element 35(1), and thereby eliminating the need for a separate ultrasonic transducer on the roving probe 16. Here, the ablation element 36 is further capable of delivering ultrasonic ablation energy to a target site. The proximity determination subsystem 48(1) also includes an ultrasound receiver 96 coupled to the ultrasound transducer proximity element 25(1). Alternatively, as previously discussed, the mapping elements 24 may be ultrasound transducers, thereby eliminating the need for proximity element transducers 25(1) separate from the mapping elements 24.

The proximity determination subsystem 48(1) also includes a host processor 98. The processor 98 directs the transmission by the proximity element 35(1), or the ablation element 36 if the element 36 is an ultrasonic transducer, of an ultrasonic field. The receiver 96 detects the receipt by each proximity element 25(1) of the ultrasonic pulses emitted by the proximity element 35(1) (or the ablation element 36 incorporating an ultrasonic transducer). The host processor 98 analyzes the detected ultrasonic pulses and calculates the time delays for the proximity element 25(1) associated with each mapping element 24 of the mapping probe 14. Given the time delays and the known velocity of sound in the blood pool, assuming the three-dimensional space within which the present invention is operating is inside a patient's body, the host processor 98 derives the distance between each proximity element 25(1) of the mapping probe 14 and the proximity element 35(1) of the roving probe 16. The host processor 98 preferably continually performs this detection process for real time determination of the proximity of the proximity elements 35(1), 25(1). As the time delays between the time the proximity element 35(1) transmits an ultrasonic signal and the time a proximity element 25(1) receives the signal grow shorter, the processor 98 determines that the proximity elements 35(1) and 25(1) are progressively closer to each other.

2) Impedance Sensing Detection Mode

Figure 6:
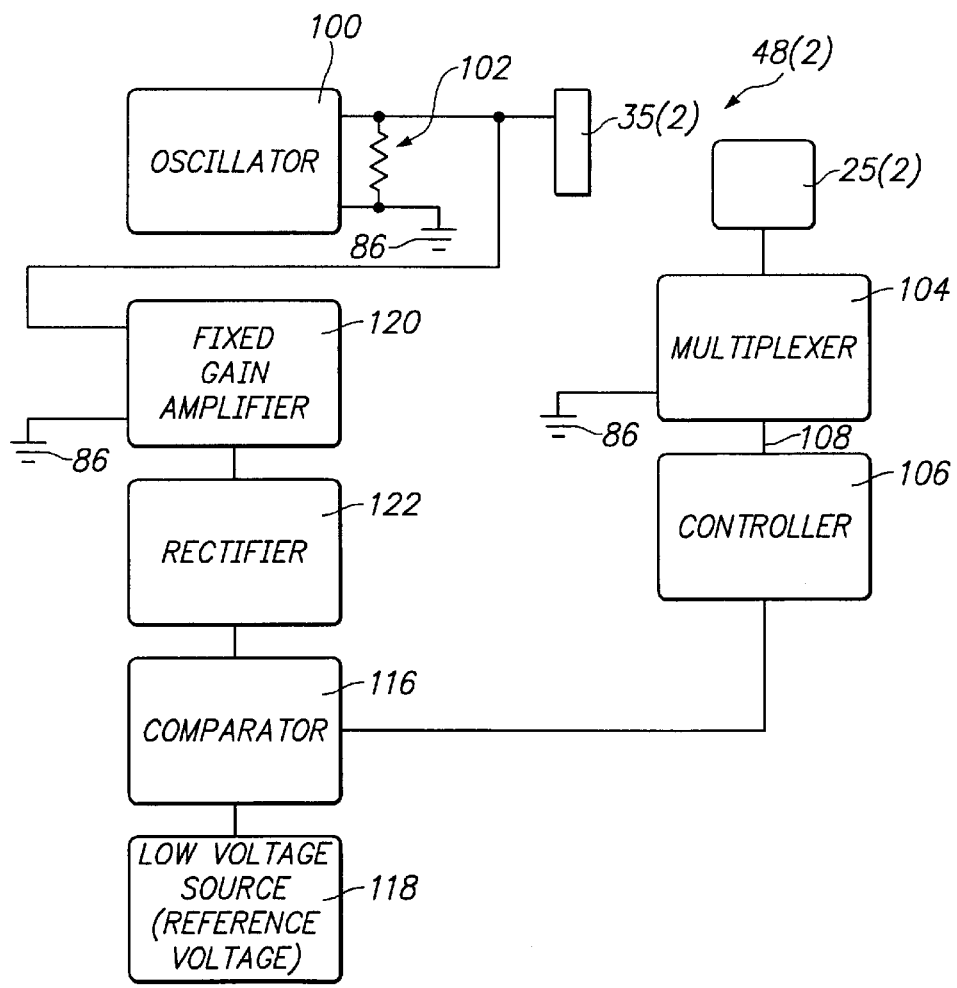
FIG. 6 shows a proximity determination subsystem implementing impedance sensing for locating purposes.

FIG. 6 shows another proximity determination subsystem 48(2), which employs impedance or contact sensing to indicate when the proximity element 35(2) of the roving probe 16 is in very close proximity to (for example, within 1 to 2 mm) or actually touching a proximity element 25(2) of the mapping probe 14. Impedance sensing can be used in combination with ultrasound time-delay sensing, thereby augmenting general real time guidance with great accuracy to finally locate the proximity of the proximity elements 35(2), 25(2). Alternatively, impedance sensing may be used by itself, i.e., in lieu of any of the other proximity determination subsystems described herein. In one embodiment, the proximity elements 25(2), 35(2) may be incorporated into the ablation 36 and mapping 24 elements.

The proximity determination subsystem 48(2) includes an oscillator 100, which provides a constant, relatively small current (which can range, for example, between 0.1 mAmp to about 5 mAmp) at a selected frequency (which can, for example, range from about 5 kHz to 100 kHz, and preferably is about 16 kHz). Currents substantially above about 5 mAmp and frequencies substantially below 5 kHz pose the danger of inducing fibrillation.

The oscillator 100 is coupled to the proximity element 35(2) of the roving probe 16 and to a dummy resistor load 102 (which is in the neighborhood of about 1.0 kohm). This resistor load 102 is coupled at the other end to an isolated patient ground 86. The oscillator 100 injects current having a zero d.c. component through the proximity element 35(2).

The proximity determination subsystem 48(2) includes a multiplexer (MUX) 104 electrically coupled to each proximity element 25(2). A controller 106 is also electrically coupled to the MUX 104 via an address/control bus 108. The controller 106 operates the MUX 104 to switch in sequence each proximity element 25(2) to the isolated patient ground 86.

The proximity determination subsystem 48(2) further includes a comparator 116. The comparator 116 receives input from a desired threshold low voltage source 118 (e.g., one which supplies a voltage in the neighborhood of 1.0 volt). The comparator 116 also receives as input the voltage drop between the proximity element 35(2) of the roving probe 16 and ground 86 as the MUX 104 switches in sequence through the proximity elements 25(2) of the mapping probe 14. The voltage drop is amplified by a fixed gain amplifier 120 (e.g., having an amplification factor of about x2 to x3) and rectified by a rectifier 122, which presents the peak amplitude value to the comparator 116. The comparator 116 compares the threshold voltage from the source 118 to the voltage drop between the proximity element 35(2) of the roving probe 16 and ground 86 for each proximity element 25(2) of the mapping probe 14 switched by the MUX 104.

When the proximity element 35(2) of the roving probe 16 is not sufficiently close to any proximity element 25(2) of the mapping probe 14, the impedance of any liquid in the three-dimensional space examined, such as, e.g., blood in the heart, (through which the constant current field emitted by the ablation element 36 flows) creates a higher voltage drop for each switched proximity element 25(2). This higher voltage drop is in excess of the voltage of the threshold source 118. The comparator 116 generates no output. The higher voltage drop between the proximity element 35(2) and the proximity elements 25(2) will persist when they are spaced too far apart for impedance purposes, even when the proximity elements 35(2) and 25(2) are spaced close enough together to generate location specific output based upon, for example, ultrasonic information if the contact/impedance sensing system is used with a ultrasound system.

On the other hand, once the proximity element 35(2) comes in very close proximity to one of the proximity elements 25(2) (e.g., which has experimentally been determined in the neighborhood of about 1 to 2 mm), the reduced impedance of the blood pool path (assuming the examined three-dimensional space is with the heart or body cavity containing blood) creates a voltage input for the comparator 116 that is at or below the threshold voltage of the source 118. The comparator 116 generates an output when the sensed voltage drop between the proximity element 35(2) and a switched proximity element 25(2) of the mapping probe 14 equals or drops below the set threshold level.

When this occurs, the controller 106 registers from the MUX 104 the particular proximity element 25(2) of the mapping probe 14 at which the low voltage drop condition was created. This indicates that the proximity element 35(2) is in close proximity to one of the proximity elements 25(2) of the mapping probe 14.

During the short switching intervals of the MUX 104 (e.g., which are typically in the range of 1 micro-second or less), no proximity element 25(2) of the mapping probe 14 is connected to ground 86. The impedance of the proximity element 35(2) of the roving probe 16 with respect to ground 86 therefor becomes high when switching occurs, creating a transient high voltage drop condition. The dummy resistor load 102 of the oscillator limits the transient voltage, thereby preventing the onset of fibrillation.

Impedance sensing can also be used in conjunction with fluoroscopy or other direct imaging technologies. Additionally, in one embodiment of the proximity determination subsystem 48(2), the ablation element 36 acts as the proximity element 35(2), thereby eliminating the need for a separate proximity element 35(2). In another embodiment, the mapping elements 24 act as the proximity elements 25(2), thereby eliminating the need for separate proximity elements 25(2). In yet another embodiment, both the proximity elements 35(2), 25(2) are incorporated into the ablation element 36 and the mapping elements 24, respectively.

3) Conduction Delay Sensing Mode

Figure 7:
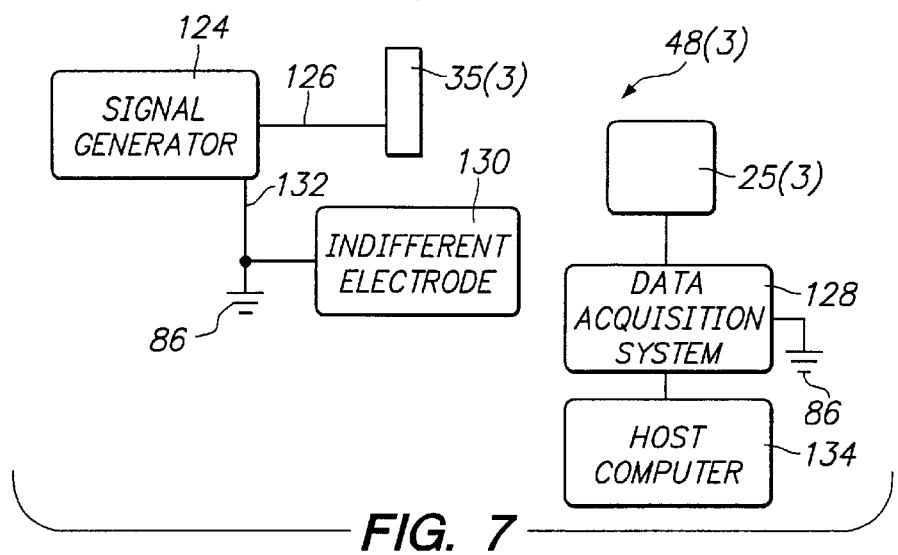
FIG. 7 shows another proximity determination subsystem that locates the functional element of the second probe relative to the functional elements of the first probe by sensing the timing of depolarization events in heart tissue resulting from a stimulating pacing signal.

FIG. 7 shows another proximity determination subsystem 48(3), which locates a proximity element 35(3) of the roving probe 16 relative to the proximity elements 25(3) by sensing the timing of depolarization events in heart tissue resulting from a stimulating pacing signal, if the three-dimensional space within which the proximity data is to be determined is in the heart. As with the subsystem 48(2), the proximity elements 25(3), 35(3) may be integrated with the ablation 36 and mapping 24 elements.

The proximity determination subsystem 48(3) includes a pulse generator 124 having a supply path electrically coupled to the proximity element 35(3). An indifferent electrode 130 is coupled to the return path 132 of the pulse generator 124. The proximity determination subsystem 48(3) also includes a data acquisition system (DAQ) 128. The DAQ 128 is further electrically coupled to the proximity elements 25(3) of the mapping probe 14 and the isolated patient ground 86.

The DAQ 128 receives and processes electrical activities sensed by the proximity elements 25(3) in the form of electrograms. A host computer 134 is coupled to the DAQ 128 for processing the electrograms to derive a location specific output. The mapping processing system 32 (shown in FIG. 14) is capable of mapping the heart region to identify foci using electrograms. Therefore, in the implementation of proximity determination subsystem 48(3), the same mapping processing system 32 that maps the heart region based upon electrograms to locate an appropriate treatment site, can also be used as a substitute for the host computer 134 and DAQ 128.

Turning back to the embodiment shown in FIG. 7, the signal generator 124 injects a pacing signal through the proximity element 35(3) into the myocardium contacting the proximity element 35(3). The pacing signal is returned to the pulse generator 124 by the indifferent electrode 130. The pacing signal provides enough voltage or current to the proximity element 35(3) to locally stimulate the myocardium. Still, the pacing signal is not large enough to field stimulate the myocardium at a distance greater than about 2 mm. In the preferred implementation, it is believed that the pacing signal should be about 3 milliamps (3 Volts), with a pulse width of about 0.5 msec. Furthermore, the rate of the pacing signal is faster than the baseline heart beat (that is, typically greater than about 70 beats per minute). Preferably, the pacing rate should be at least 20% higher than the baseline heart beat (that is, typically greater than 84 beats per minute).

As is well known, the pacing signal depolarizes viable myocardial tissue at the site of the proximity element 35(3). The intensity of the electric field generated by the pacing signal decreases with the square of the distance from the proximity element 35(3), so the pacing signal will not be effective unless the proximity element 35(3) is very near or in intimate contact with viable myocardium. Therefore, to effectively use the proximity determination subsystem 48(3) to generate the location specific output, it is preferably to assure by fluoroscopy or other appropriate methodology that the proximity element 35(3) is in electrical contact with the myocardium.

Figure 8:
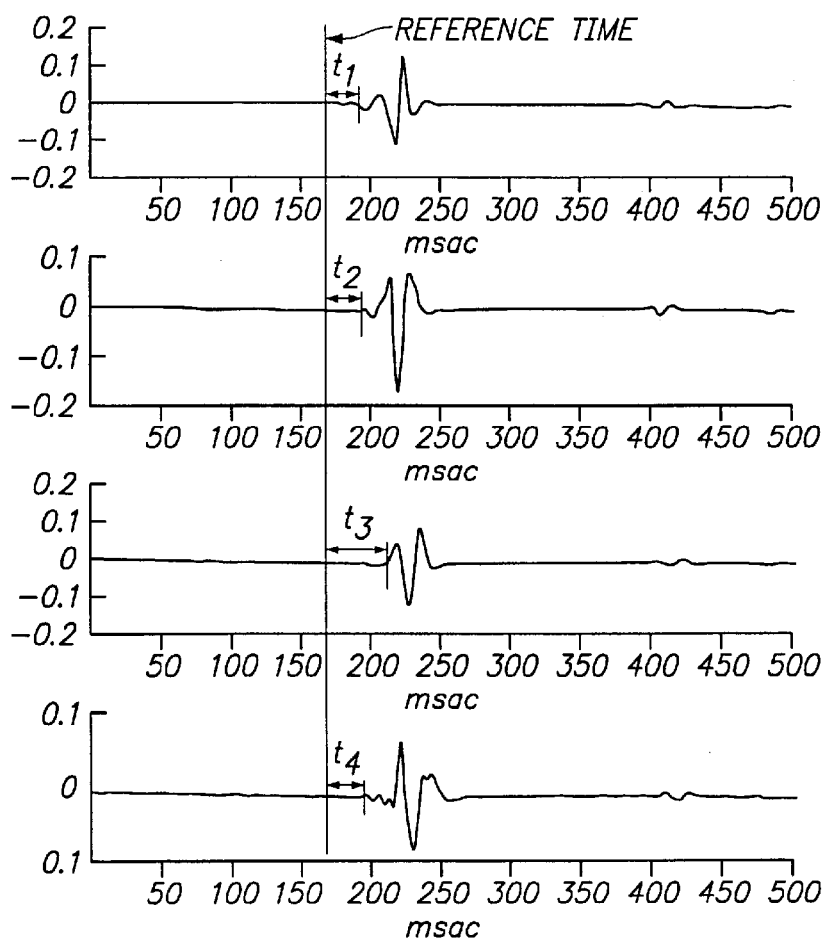
FIG. 8 shows four representative electrograms associated with the proximity determination subsystem of FIG. 7.

The proximity elements 25(3) of the mapping probe 14 will each sense an electrical event as the depolarization front generated by the pacing signal reaches them. The DAQ 128 receives the sensed electrical events, which are processed by the host computer 134 for viewing as electrograms (see FIG. 8, which shows four representative electrograms for illustration purposes). In conventional fashion, the DAQ 128 preferable filters or removes significant pacing artifacts that could interfere with the analysis of the electrograms.

A reference time for analyzing the electrograms is chosen, for conventional electrogram beat clustering purposes. This may be manually chosen or input by a user or physician. The activation delay is measured between the pacing pulse and the earliest depolarization event (shown as $t_1$, $t_2$, $t_3$, and $t_4$ in FIG. 8). For all the beats in the selected cluster, the user may manually select the earliest depolarization event for each proximity element 25(3) of the mapping probe 14. The host computer 134 creates a matrix of the computed activation delays based upon the selected depolarization event.

Alternatively, the host computer 134 can electronically analyze the electrograms to detect the earliest depolarization events. This implementation (not shown) includes a high pass filter to remove low frequency components from the electrograms, especially the direct current signal, a squaring function to make the signal positive, and a thresholding technique to determine the activation point. This implementation could also implement a windowing function before the thresholding function.

After the activation points are determined, the host computer 134 calculates the time differences between the activation point of each proximity element 25(3) of the mapping probe 14 and the activation time of the pacing pulse emitted by the proximity element 35(3) of the roving probe 16. The proximity element 25(3) having the smallest time difference between the pacing signal and its activation point is the proximity element 25(3) nearest to the proximity element 35(3) of the roving probe 16. The amplitude of the pacing artifact can also be analyzed to determine the closeness of the proximity element 25(3) to the proximity element 35(3).

In an alternative implementation, the proximity determination subsystem 48(3) emits a pacing pulse through a proximity element 25(3) of the mapping probe 14, typically the one closest to the target site by the mapping processing system 32 (discussed herein). The system 48(3) senses the electrical event generated by the pacing pulse at the proximity element 35(3) of the roving probe 16. Alternatively, the proximity element 35(3) of the roving probe 16 could be used as the emitter and a proximity element 25(3) of the mapping probe 14 as the sensor.

In either situation, the host computer 134 may continuously calculate the time differences between the pacing pulse and the sensed local depolarization event, as the user moves the proximity element 35(3). For example, as proximity element 35(3) moves progressively closer to a proximity element 25(3) of the mapping probe 14, the time delays get progressively shorter, and vice versa.

4) Iterative Voltage Analysis

Figure 9:
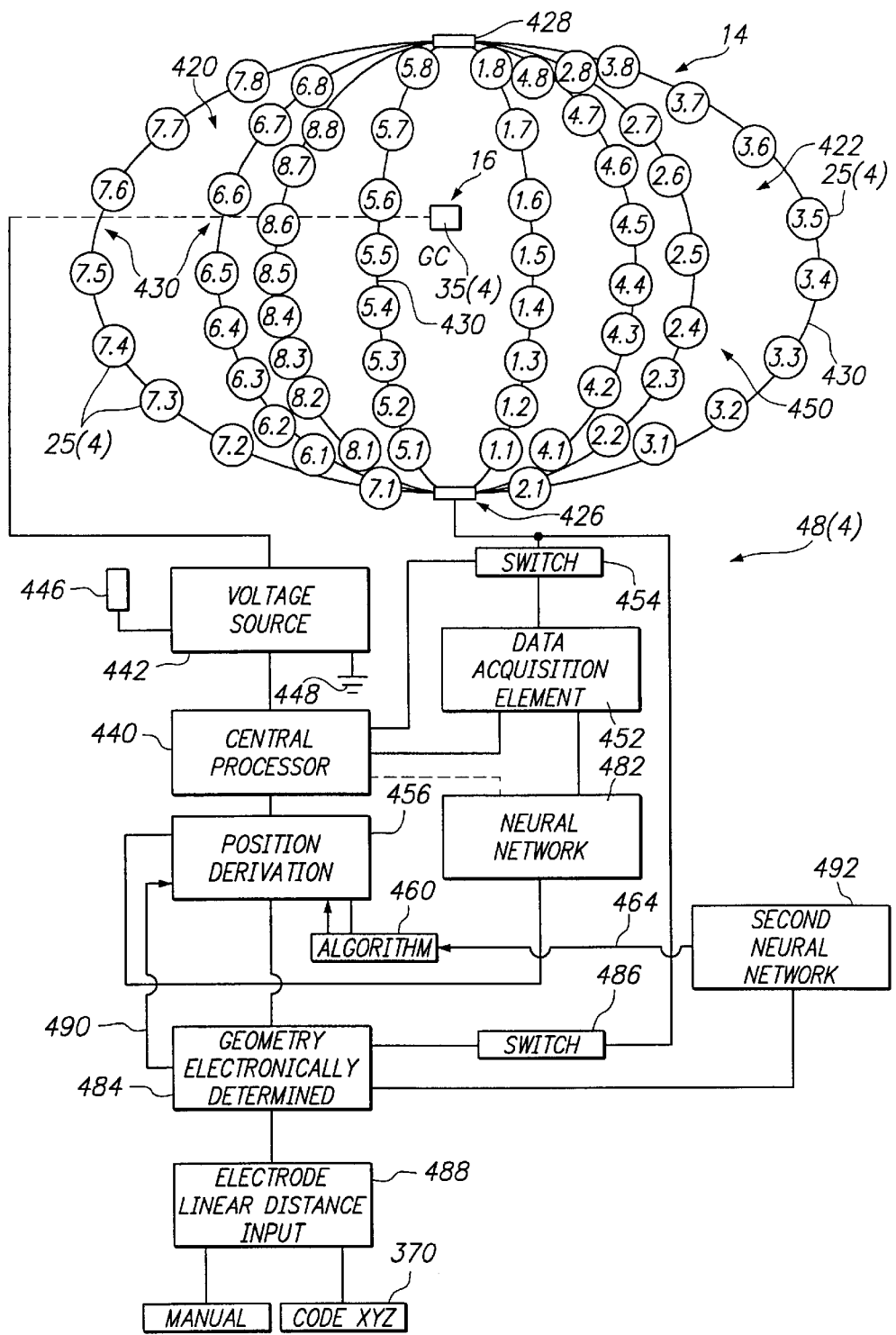
FIG. 9 illustrates a proximity determination subsystem that uses an iterative differential voltage analysis to determine the proximity of a functional element located on a second probe relative to a first probe.

FIG. 9 shows another proximity determination subsystem 48(4), which conducts an iterative differential voltage analysis to determine the proximity of the proximity element 35(4) of a roving probe 16 relative to proximity elements 25(4) of a mapping probe 16. The mapping probe 16 shown in FIG. 9 includes eight splines 430, and each spline 430, in turn, carries eight proximity elements 25(4), for a total of sixty-four proximity elements 25(4) positioned about the space 422. In one embodiment, the proximity elements 25(4) are electrodes. In another embodiment, the proximity elements 25(4) are incorporated into the mapping elements 24, thereby eliminating the need for separate proximity elements 25(4). Similarly, an ablation element 36 on the roving probe 16 may incorporate proximity element 35(4), eliminating the need for a separate proximity element 35(4). FIG. 9 identifies the proximity elements 25(4) by the designation (A,B), where A=1 to p and B=1 to e, where p is the total number of splines 430 and e is the number of proximity elements 25(4) on each spline 430 (in the illustrated embodiment, p=8 and e=8).

The proximity determination subsystem 48(4) includes a central processing unit 440, which couples a voltage source 442 to the proximity element 35(4). In FIG. 9, an indifferent electrode 446, carried as a patch on the exterior of the patient, comprises the voltage return, which is, in turn, coupled to isolated or patient ground 448. Alternatively, another electrode carried by the mapping probe 16 can serve as the voltage return. The proximity element 35(4) creates a voltage field 450 within the space 422, which varies in detected amplitude at each proximity element 25(4) according to its distance from the proximity element 35(4).

The proximity determination subsystem 48(4) includes a data acquisition element 452 coupled to the central processing unit 440 and to a switch element 454. The switch element 454 individually conditions each proximity element 25(4) (A,B) to sense voltage existing at its location within the field 450, which the data acquisition element 452 samples and holds. The operation of an exemplary data acquisition element is described in U.S. Pat. No. 6,095,150, which is incorporated by reference herein.

Figure 10:
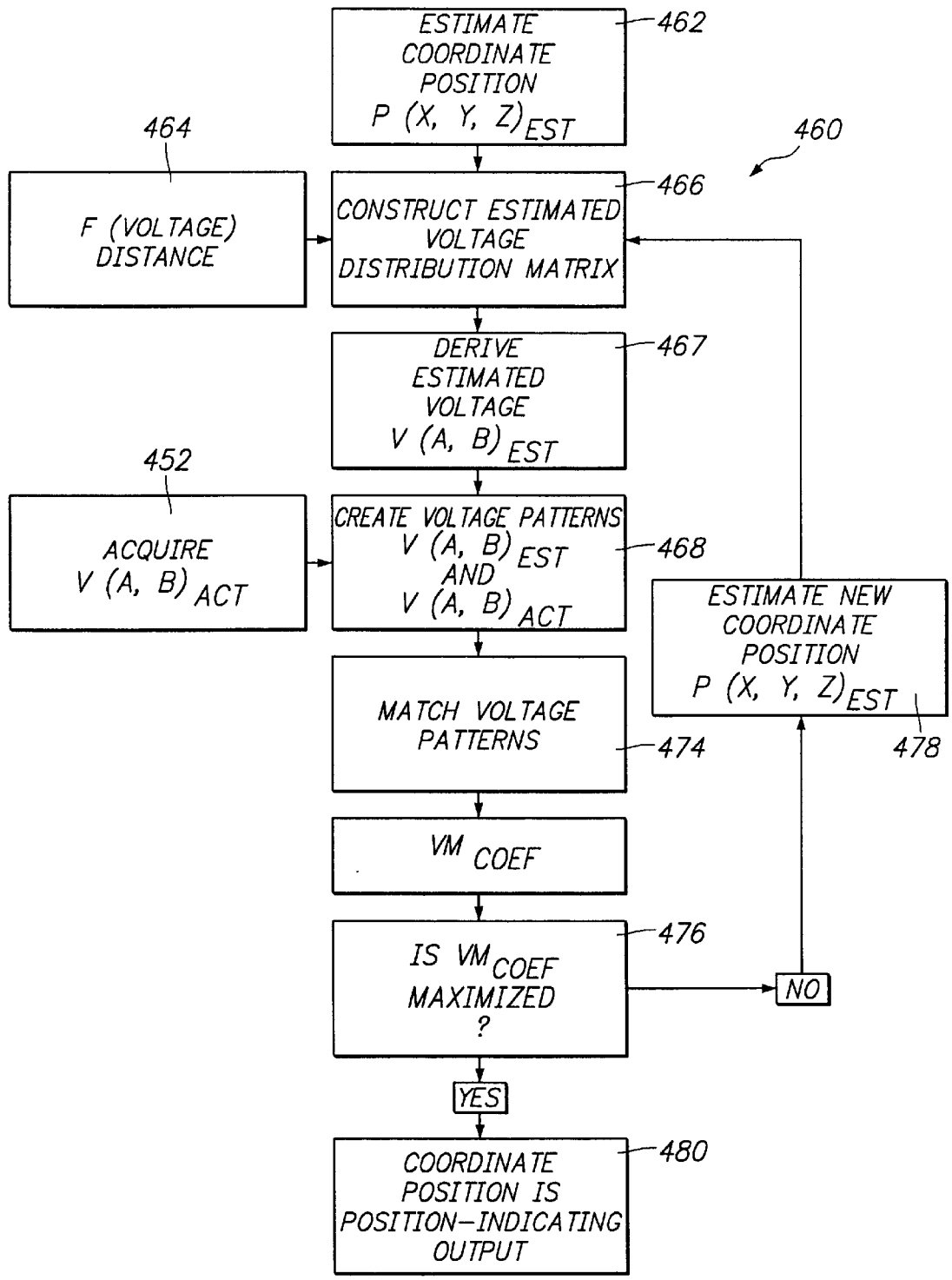
FIG. 10 shows an iterative process suitable for use by the proximity determination subsystem of FIG. 9.

The central processing unit 440 includes a processing component 456 that derives a position-indicating output based upon the voltage distribution sensed by the proximity elements 25(4) (A,B). FIG. 10 shows the steps of a preferred algorithm 460 for deriving the output. The algorithm 460 includes, as a first step 462, establishing an estimated coordinate position $P(x, y, z)_{EST}$ for the proximity element 35(4) on the roving probe 16 within the space 422, where x is the x-field coordinate, y is the y-field coordinate, and z is the z-field coordinate.

For example, $P(x, y, z)_{EST}$ can be initially arbitrarily set at P(0,0,0), which is at the geometric center of the voltage field 450 (designated as GC in FIG. 9). Alternatively, differential waveform analysis, or differential voltage analysis, or amplitude analysis, as described, e.g., in U.S. Pat. No. 6,095,150, alone or in combination, can also be used to more accurately estimate $P(x, y, z)_{EST}$. To increase processing efficiencies, multiple signals that are orthogonal from a signal processing standpoint (for example, waveform signals of different frequencies, waveform signals of the same frequency but which differ by 90 degree in phase, and waveforms from unrelated white noise sources) may be transmitted simultaneously, as described in U.S. Pat. No. 6,095,150, which has already been incorporated by reference.

In the next step 466, the algorithm 460 computes the distance DD(A,B) between each proximity element 25(4) (A,B) and the proximity element 35(4) at $P(x,y,z)_{EST}$. The distances DD(A,B) can be normalized to facilitate analysis. The algorithm then applies a preestablished, mathematical voltage-to-distance function 464 to derive the estimated voltage $V(A,B)_{EST}$ at each proximity element 25(4) (A,B), based upon DD(A,B). In effect, the algorithm 460 constructs an estimated voltage distribution matrix, which would exist, according to the function 464, if $P(x, y, z)_{EST}$ was the actual voltage transmission point. The voltage-to-distance function 464 can be empirically determined or be based upon finite element analysis and stored in memory accessible to the central processing unit 442. In the next step 467, the algorithm 460 derives an estimated or expected voltage differential $V(A,B)_{EST}$ for each proximity element 25(4).

Figure 13:
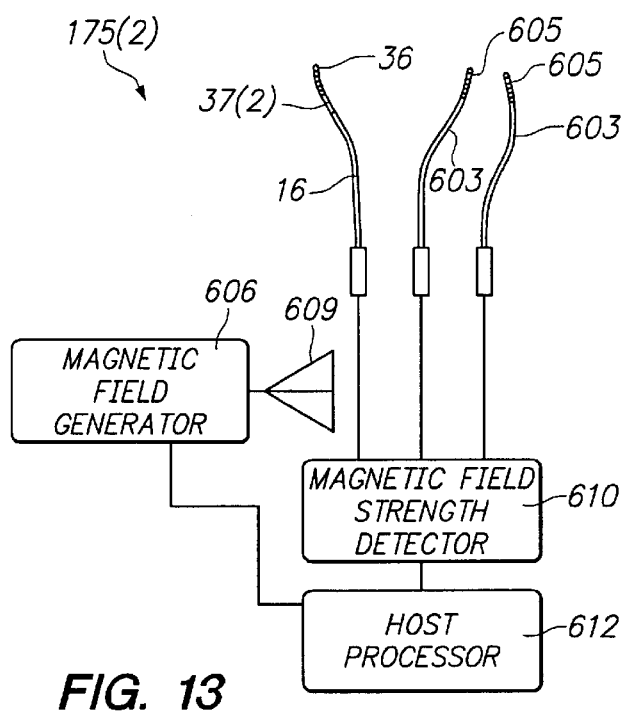
FIG. 13 illustrates a precise location determination subsystem that utilizes magnetic field strength triangulation techniques.

In the next step 468, the algorithm 460 receives as input $V(A, B)_{ACT}$, where $V(A, B)_{ACT}$ is the measured voltage value acquired by operation of the data acquisition element 452 at each proximity element 25(4) (A,B). As FIG. 13 shows, the algorithm 460, in this step 468, creates a measured voltage distribution pattern 470 based upon the values for $V(A, B)_{ACT}$, which plots (on the Y-axis) the sensed voltage values for each proximity element 25(4) (numbered 1 to 64 on the X-axis). The algorithm 460 creates an estimated voltage distribution pattern 472 based upon the values for $V(A, B)_{EST}$, which plots (on the Y-axis) the estimated voltage values for each proximity element 25(4) (again numbered 1 to 64 on the X-axis).

As a next step 474, the algorithm 460 matches the voltage distribution pattern 470 with the voltage distribution pattern 472 to derive a voltage matching coefficient $VM_{COEF}$. The value of the voltage matching coefficient $VM_{COEF}$ for a given $P(x, y, z)_{EST}$ increases as $P(x, y, z)_{EST}$ coincides with the actual location of the proximity element 35(4). That is, the value of the voltage matching coefficient increases in relation to the proximity of the proximity element 35(4) to the estimated position $P(x,y,z)_{EST}$.

The central processing unit 442 can derive the matching coefficient $VM_{COEF}$ in various conventional ways, for example, by employing pattern matching, matched filtering, or cross correlation. Examples of using these techniques to derive matching coefficients appear in commonly assigned U.S. Pat. No. 5,595,183 entitled, "Systems and Methods for Examining Heart Tissue Employing Multiple Electrode Structures and Roving Electrodes," which is incorporated herein by reference.

In the next step 476, the algorithm 460 determines whether $VM_{COEF}$ is the "best," i.e., whether it is maximized under the processing rules applied. For the first iteration, and for all subsequent iterations where $VM_{COEF}$ is not maximized, the algorithm 460 applies (in step 478) a preselected incremental correction factor Dx to the x coordinate, Dy to the y coordinate, and Dz to the z coordinate of the estimated position of the proximity element 35(4) to create a new estimated position P(x+Dx, y+Dy, z+Dz)), which become the new coordinates for an estimated position $P(x,y,z)_{EST}$. The algorithm 460 then loops through the foregoing steps 466, 467, 468, 474, and 476, to derive an iterated voltage matching coefficient $VM_{COEF}$ based upon the new estimated location. The algorithm 460 iteratively selects Dx, Dy, and Dz until a best (maximum value) voltage matching coefficient $VM_{COEF}$ is achieved in step 476. The coordinates $P(x,y,z)_{EST}$ at the best, maximum voltage matching coefficient $VM_{COEF}$ become the position-indicating output, as shown in step 480 in FIG. 10.

There are various ways in which the iteration of the x-, y-, and z-coordinates can be accomplished. For example, the algorithm 460 can iterate the x-coordinate alone (keeping the y- and z-coordinates constant) until a best voltage matching coefficient $VM_{COEF}$ is achieved, then fix the x-coordinate at that value and iterate the y-coordinate alone (while also keeping the z-coordinate constant) until another best voltage matching coefficient $VM_{COEF}$ is achieved, and then fix the y-coordinate at that value and iterate the z-coordinate alone (keeping the previously fixed x- and y-coordinates constant), until another best voltage matching coefficient $VM_{COEF}$ is achieved. The algorithm 460 then loops back through this process, until the best voltage matching coefficient $VM_{COEF}$ is obtained for each local x-, y-, and z-coordinate, as well as for $P(x, y, z)_{EST}$ overall. Alternatively, the x-, y-, and z-coordinates, can be simultaneously incremented to maximize the voltage matching coefficient $VM_{COEF}$ for $P(x,y,z)_{EST}$, using, for example, a conventional maximum gradient method.

Figure 11:
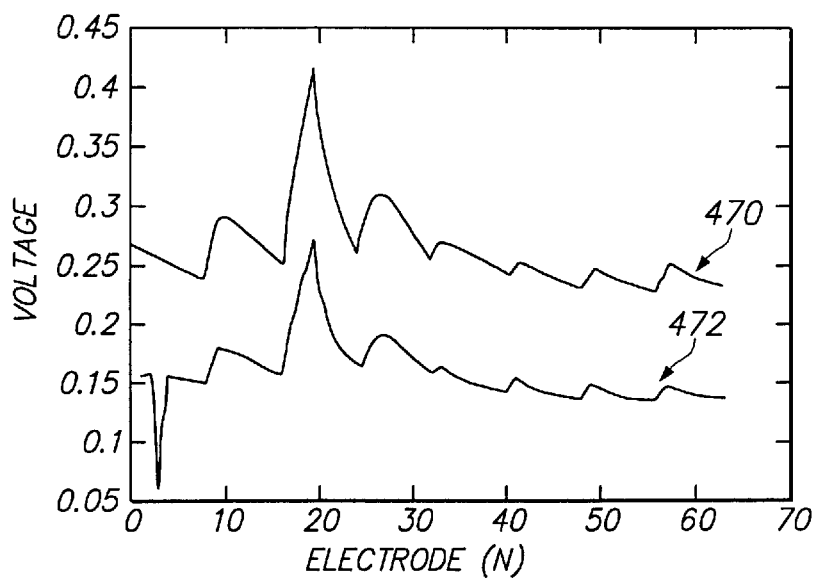
FIG. 11 shows a measured voltage distribution pattern and an estimated voltage distribution pattern generated by the proximity determination subsystem of FIG. 9.

An example of a measured voltage distribution pattern 470 and an estimated voltage distribution pattern 472 generated by the proximity determination subsystem 48(4) is shown in FIG. 11.

Due to its iterative nature, the algorithm 460 shown in FIG. 10 corrects for distortion of the mapping probe and roving probe caused by exposure to dynamic conditions within a body cavity, such as within a beating heart chamber. The iterative nature of the algorithm 460 also corrects for electrical "noise" caused, for example, by the inherent electrical resistance of mapping elements 24 and proximity elements 25(4), 35(4), such as electrodes and associated electrical wiring. Further, the algorithm 460 corrects for dynamic conditions related to a body cavity caused by any movement of the patient's body.

Furthermore, the iterative differential voltage analysis just described also makes possible the generation of an error signal, should the position of the proximity element 35(4) stray beyond the energy field 450. Should this event occur, the estimated voltage and the actual voltage become mirror images. This outcome, when sensed by the central processing unit 442, can command the generation of an out-of-field error signal.

In an alternative embodiment, the central processing unit 442 can incorporate a neural network 482 (see FIG. 9), which has been trained on experimentally acquired sets of voltage distribution data related with known positions of the proximity element 35(4). Once the training phase is completed, the network 482 can instantaneously output the position-indicating output, based upon input from the data acquisition element 452 of voltage distribution data sensed by the proximity elements 25(4) during transmission of voltage by the proximity element 35(4).

5) Cardiac Morphology Proximity Determination Subsystem

An analysis of cardiac signal morphology may be utilized with the proximity determination subsystem 48 to determine the proximity of the roving probe 16 to the mapping probe 14. First, an electrogram for the patient's cardiac cycle is generated using known methods. Those skilled in the art would recognize that the electrogram reflects the morphology of the patient's heart. The mapping probe 14 is placed at a predetermined location with the heart, in this case within the right atrium and at substantially the tricuspid isthmus. The roving probe 16 is placed within the heart and, to locate and guide the movement of the roving probe 16 relative to the mapping probe 14, the proximity determination subsystem 48 records a voltage signal from at least one of the proximity elements 25 disposed on the mapping probe 14. The proximity determination subsystem 48 then records a voltage signal from the proximity element 35, or the ablation element 36 if it incorporates the proximity element 35, of the roving probe 16. The proximity determination subsystem 48 compares the voltage signals recorded from a proximity element 25 and the proximity element 35 with the electrogram to determine the proximity of those proximity elements 25, 35. For example, correlation techniques can be employed to determine how closely the voltage signal acquired by proximity element 35 of the roving probe 16 resembles the voltage signal acquired by a proximity element 25 of the mapping probe 14. The greater the correlation between the two voltage signals, the closer proximity element 35 is located to a proximity element 25. The proximity elements 25 and 35 in the aforementioned embodiment are preferably electrodes.

B. The Precise Location Determination Subsystem

Referring to FIG. 14, the system 10 includes a precise location determination subsystem 175 that is coupled to the roving probe 16. The precise location determination subsystem 175 determines a precise three dimensional position of a location element 37 carried by the roving probe 16 with respect to a three-dimensional coordinate system. For example, the location element 37 can be a location sensor, in which case, a transmitting antenna located outside of the body can be used to generate a field (e.g., magnetic or ultrasonic) that is detected by the location sensor, thereby providing information to the precise location determination subsystem 175 sufficient to determine an absolute position of that sensor with respect to a coordinate system associated with the antenna. For embodiments of the precise location determination subsystem 175 using magnetic or ultrasonic fields, the location element 37 is a magnetic sensor or an ultrasonic transducer, respectively. For other embodiments of the precise location determination subsystem 175, the location element 37 may also be an electromagnetic sensor, when electromagnetic fields are utilized, or an optic element, when, e.g., a video camera tracking system is used. Also, wireless location sensors, such as, e.g., electromagnetic or magnetic resonant transducers, electronic emitters, infra- or near-infrared emitters, can be used. In this case, the link between the location element 37 and the location determination subsystem 175 can be a wireless link.

Preferably, the precise location determination subsystem 175 determines the absolute location of a location element 37 that is disposed on the distal portion of the roving probe 16. The location element 37 may be incorporated into ablation element 36 and/or the proximity element 35, or may be a separate component entirely. Furthermore, the location element 37 is preferably an array of individual, discrete sensors oriented to provide x, y, z, yaw, roll, and pitch coordinate data in order to enable the precise location determination subsystem 175 to determine the orientation of the location element 37, and thus the roving probe 16. The location determination subsystem 175 can process and provide position specific information in various ways. Further details on such localization techniques are disclosed in PCT Publication WO 00/10456, entitled, "Intrabody Navigation System for Medical Application," which is expressly and fully incorporated herein by reference.

Figure 12:
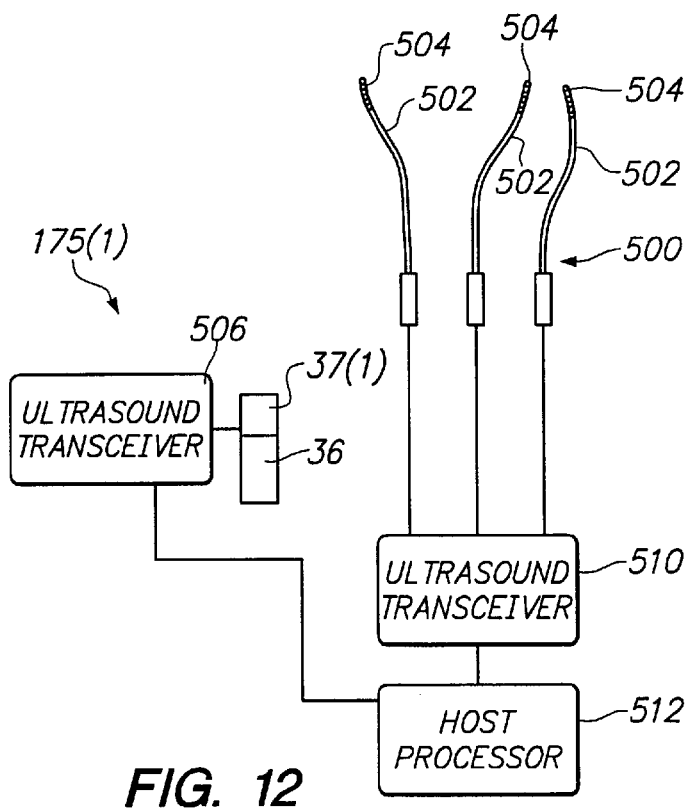
FIG. 12 illustrates a precise location determination subsystem that utilizes ultrasonic signal triangulation techniques.

In one embodiment, shown in FIG. 12, ultrasound triangulation techniques are utilized by an ultrasound precise location determination subsystem 175(1) to determine the absolute position of a location element 37 carried by the roving probe 16. Here, the location element is an ultrasonic transducer location element 37(1). For example, the time of flight of a sound wave transmitted from the location element 37(1) located on the roving probe 16 relative to transducers 504 located on other catheters 502, on the body, or on reference points outside of the body is determined. Triangulation techniques are then utilized in order to render an absolute location, including orientation, of the location element 37(1) of the roving probe 16 with respect to a three-dimensional coordinate system. Subsystem 175(1) is discussed in detail below.

In another embodiment, shown in FIG. 13, magnetic field locating techniques are utilized by a magnetic precise location determination subsystem 175(2) to determine the absolute position of a location element 37 carried by the roving probe 16. Here, the location element is a magnetic sensor location element 37(2). Location element 37(2) is preferably an array of magnetic sensors. For example, in one embodiment, the location element 37(2) is an array of six magnetic coil sensors, with one coil sensor oriented to provide one of the x, y, z, yaw, roll, and pitch coordinates for the location element 37(2). Reference magnetic sensors 605 are placed either in the three-dimensional space, on the body, or on some location outside of the body. An antenna 609 transmits magnetic fields. The magnetic fields received by location element 37(2) and reference sensors 605 are analyzed to determine the precise or absolute location and orientation of the roving probe 16 in space. The location element 37(2) may be separate from the ablation element 36, as illustrated in FIG. 13, or the ablation element 36 may include a magnetic sensor, thereby eliminating the need for a separate location element 37(2). Subsystem 175(2) is discussed in detail below.

In an alternative embodiment, the precise location determination subsystem 175 determines a precise three dimensional position of one or more location elements 37 carried by the mapping probe 14 with respect to a three-dimensional coordinate system. Although the construction of the mapping probe 14 may limit the number of location elements 37 that it can carry, the location elements 37 can be strategically placed on select portions of the mapping probe 14 to provide orientation data for the distal portion of the mapping probe 14. For example, if the mapping probe 14 includes a distal 3-D catheter structure 20a, as illustrated in FIG. 2a, the mapping probe 14 can include a location element 37 disposed proximally near the base member 26, a location element 37 disposed distally near the end cap 28, and a location element 37 disposed on one spline 30 (not shown). As will be discussed in further detail, knowledge of the orientation of the distal structure 20 of the mapping probe 14 enables the map registration subsystem 1000 to more accurately determine the absolute positions of the mapping elements 24 in the three-dimensional coordinate system. Additionally, if the distal structure 20 is subject to geometric distortion, the location elements 37 can be used to determine the nature of this distortion, thereby providing further information to more accurately determine the absolute locations of the mapping elements 24.

Representative modes of operation for the precise location determination subsystem 175 will now be described.

1) Ultrasound Precise Location Determination Subsystem

In the embodiment of the precise location determination subsystem 175(1) shown in FIG. 12, ultrasound triangulation techniques are utilized in order to render a precise, or absolute, three dimensional location of a location element 37(2), which is an ultrasound transducer, of the roving probe 16. The precise location determination subsystem 175(1) further includes a plurality of ultrasonic transducers 504 disposed on a plurality of reference catheters 502 insertable within the patient's body. In other embodiments, the transducers 504 are positioned on a patient's body or at locations external to the body.

In the illustrated embodiment of the precise location determination subsystem 175(1), the roving probe 16 (not illustrated) further comprises the location element 37(1) in addition to, and preferably carried on or near, the ablation element 36. Alternatively, the ablation element 36 may include an integrated ultrasound transducer, thereby eliminating the need for a separate location element 37(1), i.e., there is no need for a separate location element 37(1) in this embodiment since the ablation element 36 also functions as the location element 37(1). Turning back to the embodiment shown in FIG. 12, the location element 37(1) is in operable connection with an ultrasound transceiver 506. Additionally, a plurality of reference transducers 504 are included with the subsystem 175(1). The reference transducers 504 are disposed on catheters 502, or at other locations in or on the body, such as, e.g., on a patient's chest or at fixed points away from the body. In a preferred embodiment, the reference catheters 502 are insertable into a three-dimensional space in order to provide a plurality of reference points within the three-dimensional space. The three-dimensional space may be a space within a patient's body. As with the orientation of the location element 37(1) on the roving probe 16, the ultrasound transducers 504 of the reference catheters 502 are preferably disposed towards the distal tip of the catheters 502. The transducers 504 of the reference catheters 502 are coupled to an ultrasound transceiver 510. Suitable transducers include, but are not limited to, phased array transducers, mechanical transducers, and piezoelectric crystals. In an alternative embodiment, the location element 37(1) and the reference transducers 504 may be coupled to a single ultrasound transceiver, thereby eliminating the need for two ultrasound transceivers.

The precise location determination subsystem 175(1) also includes a host processor 512 that is in operable connection with the ultrasound transceivers 506 and 510. The host processor 512 and the ultrasound transceivers 506 and 510 may be contained within one integrated unit or, alternatively, may be separate and discrete components. The host processor 512 further comprises control circuits that cause the location element 37(1) and the transducers 504 to vibrate and produce ultrasound waves. The transceivers 506, 510 transmit and receive the ultrasonic signals that are sent to and received from the location element 37(1) and the transducers 504. The ultrasound signals that are transmitted by the location element 37(1) and the transducers 504 travel through the patient's body. Subsequently, a portion of the signals generated by the location element 37(1) of the roving probe 16 will be reflected back from a bodily structure and impinge, i.e., be received by, the location element 37(1). These signals are not, however, processed because location element 37(1) is not in listening mode at this time. Transducers 504 are, however, in listening mode. When in listening mode, the location element 37(1) of the roving probe 16 will also receive ultrasound signals that were generated by the transducers 504 located on the reference catheters 502. The location element 37(1) generates electrical signals corresponding to the ultrasound signals received from transducers 504 and then transmits the electrical signals back to the host processor 512 via the ultrasound transceiver 506. In a like manner, the transducers 504 will receive signals generated by the location element 37(1) on the roving probe 16. The transducers 504 are also capable of generating electrical signals representing the received signals and transmitting the electrical signals back to the processor 512 via transceiver 510.

The host processor 512 analyzes electrical signals corresponding to ultrasound signals received by both the location element 37(1) on the roving probe 16 and the transducers 504 of the reference catheters 502 in order to triangulate the position and orientation of the location element 37(1). The host processor 512 also compensates for the known velocity of sound in the blood pool when making the calculations, if the roving probe 16 is placed within the body. Using these calculations, the host processor 512 employs triangulation methods and determines a precise three dimensional location and orientation, i.e., an absolute location, of the location element 37(1) with respect to the three-dimensional coordinate system with the subject space or volume that is provided by transducers 504. Preferably, the host processor 512 performs these calculations on a continual basis in order to enable the real time tracking of the location element 37(1) within the patient's body.

Although three reference catheters 502 and transducers 504 are illustrated in FIG. 12, both a smaller number or a larger number of reference catheters may be utilized. A catheter 502 may also carry more than one transducer 504. For example, the use of nine reference transducers 504 would allow the host processor 512 to refine the localization of the location element 37(1) of the roving probe 16. With the implementation of nine reference transducers 504 rather than three, an amount of redundant data would be generated, thereby allowing the host processor 512 to compensate for any erroneous data such as, e.g., if one of the transducers 504 malfunctions.

In an alternative embodiment, a reference transducer or transducers suitable for placement on a surface exterior to the patient's body or actually on the surface of the patient's body may be used instead of the reference catheters 502 that are positioned within the body. Also, a plurality of reference transducers may be placed at various locations outside of the body, in lieu of the reference catheters 502 within the body, in order to provide reference points for the triangulation calculations performed by the host processor 512.

Further examples of ultrasonic triangulation techniques and systems suitable for implementation with the precise location determination subsystem are disclosed in U.S. Pat. No. 6,027,451, entitled "Method and Apparatus for Fixing the Anatomical Orientation of a Displayed Ultrasound Generated Image," which is fully incorporated herein by reference.

2) Magnetic Field Precise Location Determination Subsystem

In another embodiment of the precise location determination subsystem 175(2), illustrated in FIG. 13, magnetic field locating techniques are utilized to determine the precise three dimensional location of a location element 37(2) of the roving probe 16. A magnetic sensor location element 37(2) is placed on roving probe 16 to receive magnetic fields that are transmitted by an antenna 609. The location element 37(2) is preferably an array of individual discrete sensors, such as an array of magnetic coil sensors. Preferably, at least six sensors are included in the array that comprises the location element 37(2). With the use of at least six sensors to comprise the location element 37(2), data for the x, y, z, pitch, yaw, and roll coordinates of the location element 37(2) may be determined by the precise location determination subsystem 175(2). The location element 37(2) is preferably placed in close proximity to ablation element 36 on the distal end of the roving probe 16. Alternatively, the location element 37(2) may be incorporated into ablation element 36, thereby eliminating the need for a separate location element 37(2).

Antenna 609 is coupled to a magnetic field generator 606. The magnetic field generator 606 originates the signals that antenna 609 transmits. The magnetic field generator 606 is preferably coupled to a host processor 612, which controls the operation of generator 606. In a preferred embodiment, the antenna 609 transmits three orthogonal magnetic fields. The location element 37(2), in this embodiment, comprises several coils configured to detect the orthogonal magnetic fields transmitted by antenna 609. After detecting the orthogonal magnetic fields transmitted by antenna 609, location element 37(2) preferably transmits a signal to magnetic field strength detector 610.

As shown in FIG. 13, the magnetic field strength detector 610 is a component of subsystem 175(2) that is coupled to host processor 612. In another embodiment, however, the, magnetic field strength detector 610 may be implemented as an integral component of the host processor 612, rather than as a separate component. The magnetic field strength detector 610 relays the signal received from the location element 37(2) to the host processor 612. The host processor 612, in turn, employs the Biot-Savart law in order to compute the distance vector between the center of the antenna 609 and the location element 37(2) of the roving probe 16 based upon the signal received by the location element 37(2) and the signal transmitted by the antenna 609. The vector is next deconstructed into its x, y, and z components, as well as pitch, roll, and yaw data, in order to compute the coordinates and orientation of location element 37(2). Once the coordinates and orientation of location element 37(2) are determined, the approximate coordinates and orientation of the proximity element 35 on the roving probe 16 are also determined in embodiments where the location element 37(2) and the proximity element 35 are both disposed near each other on the roving probe 16. In an alternative embodiment, the location element 37(2) is incorporated into the proximity element 35, and the coordinates and orientation of the proximity element 35 are by necessity determined by determining the coordinates and orientation of location element 37(2). In a similar fashion, in embodiments where the location element 37(2) is incorporated into the ablation element 36, the coordinates and orientation of the ablation element 36 are by necessity determined by determining the coordinates and orientation of location element 37(2).

Figure 15:
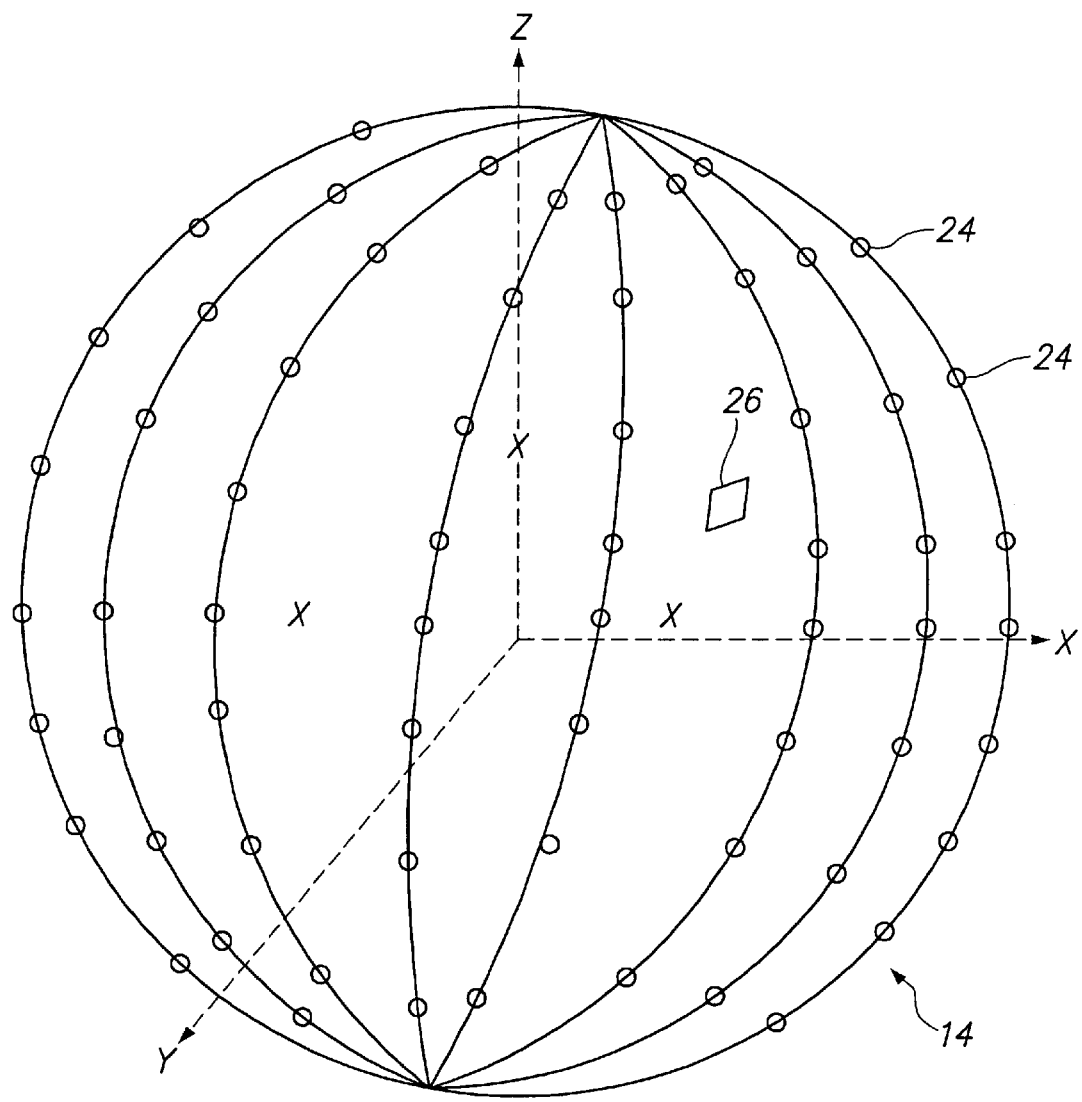
FIG. 15 illustrates a typical display generated by the present invention.

Additionally, a number of reference sensors 605 may be placed at various locations in order to minimize the effects of any motion artifacts on the localization of location element 37(2). As illustrated the reference sensors 605 are disposed on reference catheters 603 that are insertable within the body. Alternatively, the sensors 605 may be placed on an external surface of the body or on a fixed point away from the body entirely. Furthermore, although FIG. 15 shows two reference catheters 603, each having one reference sensor 605, a smaller or larger number than two reference catheters 603 may be used to vary the degree to which the localization of the roving probe 16 is refined. Additionally, each reference catheter 603 may incorporate more than one reference sensor 605 in order to further refine the localization of the location element 37(2). The reference sensors 605 are preferably coupled to magnetic field strength detector 610 and transmit signals, corresponding to received magnetic fields, to the detector 610, and subsequently to the host processor 612, in substantially the same manner as previously described with location element 37(2).

As discussed, the ablation element 36 or the proximity element 35 of the roving probe 16 may incorporate the location element 37(2), thereby eliminating the need for a separate location element 37(2). Preferably, the host processor 612 performs the aforementioned calculations, i.e., the Biot-Savart calculations, on a continual basis in order to enable the real time guidance of the ablation element 36 with respect to the three-dimensional coordinate system.

C. The Location-Proximity Association Subsystem

Referring to FIG. 14, the map registration system 1000 further comprises a location-proximity association subsystem 180 that is coupled to both the absolute location determination subsystem 175 and the proximity determination subsystem 48. Using the data from the location determination subsystem 175 and the proximity determination subsystem 48, the relational subsystem 180 relates the location and proximity data to determine absolute locations of the mapping elements 24, within the subject three-dimensional space and/or in reference to a three-dimensional reference coordinate system. That is, the relational subsystem 180 can determine the absolute position of the mapping elements 24 within the coordinate system, since it knows the absolute position of the location element 37 in the coordinate system, and the proximity between the proximity element 35 and the proximity elements 25 adjacent to the mapping element 24.

In a preferred embodiment, the location element 37 is disposed near or adjacent to the proximity element 35. Therefore, when the precise three dimensional location, and orientation, of a location element 37, which may be an ultrasound transducer or a magnetic sensor, for example, of the roving probe 16 is determined, the precise location/orientation of the proximity element 35 is by implication determined. The location-proximity association subsystem 180 analyzes the data from the location determination subsystem 175 combined with the data from the proximity determination subsystem 48, i.e., the proximity of the proximity element 35 to proximity elements 25 on the mapping probe 14, to determine the precise locations/orientations of the mapping elements 24.

For example, referring to FIG. 14, the location-proximity association subsystem 180 assigns the absolute location coordinates of the location element 37, i.e., $(x_{16}, y_{16}, z_{16})$, to a mapping element $24^i$ when it is determined that the proximity element 35 is adjacent the mapping element $24^i$, so that the coordinates $(x_{14}^i, y_{14}^i, z_{14}^i) \approx (x_{16}, y_{16}, z_{16})$. This assumes that the coordinates of the location and proximity elements 37, 35 are virtually the same, i.e., the distance between the location element 37 and the proximity element 35 is negligible, or that the location and proximity elements 37 and 35 are actually a single component. If, however, the location element 37 is a significant distance away from the proximity element 35, this distance is used to determine the actual coordinates of the proximity element 35 by adding the distance to the coordinates of the location element 37. This calculation is facilitated if the location element 37 allows the orientation of the roving probe 16 to be determined, thereby giving the distance a vector.

The location-proximity association subsystem 180 is coupled to an output display device 150 and memory 185 for displaying and storing the absolute positions of the mapping elements 24 in the coordinate system. The display device 150 can be any suitable device, e.g., a CRT, LED display, or a printer, and the memory 185 can be any suitable device, e.g., random access memory, hard disk, optical disk, and the like. The location-proximity association subsystem 180 is also coupled to the mapping processing system 32 for receiving mapping information, i.e., information associating the mapping elements 24 with targeted ablation sites. The location-proximity association subsystem 180 outputs this information to the display device 150 and memory 185 in association with the absolute positions of the mapping elements 24 to form a map of the targeted ablation sites. As illustrated in FIG. 15, a wire frame model of the mapping probe 14 is displayed relative to the reference system associated with the location determination subsystem 175. The position of elements $24^i$ on the wire frame model of the reference mapping probe 14 can be further refined by iterating the proximity detection process. The first representation of the wire frame model of the mapping probe 14 is based on known constructional details.

The system 10 is able to guide a user to place the ablation element 36 of the roving probe 16 at a target site previously identified by a suitable mapping process. The precise location/orientation of the ablation element 36 is known since the precise location of the location element 37 is known and the ablation element 36 and location element 37 are in close proximity on the roving probe 16, or are a known distance from each other. The physician is then able to guide the ablation element 36 towards the targeted ablation sites X presented on the display 150. The display 150 preferably presents the described position-identifying outputs in a real-time format most useful to the physician for remotely guiding the roving probe 16, i.e., the positions of the targeted ablation sites X, the mapping elements 24, and the ablation element 36 are continually updated in real-time by the location-proximity association subsystem 180.

4. Operation of the System

One preferred method of operating the system 10 will now be described. Using known methods, the mapping probe 14 and roving probe 16 are introduced into the patient's body and guided to a volume of interest within the patient's body, and specifically, within a chamber of the heart, as illustrated in FIG. 1.

Once the mapping and roving probes 14 and 16 are properly situated within the volume, the proximity determination subsystem 48 is operated to determine the distance of the proximity element 35 on the roving probe 16 to one of the proximity elements 25 on the mapping probe 14. Any of the aforementioned embodiments of the proximity determination subsystem 48 may be used to perform this step. Using the proximity data provided by the proximity determination subsystem 48, the physician guides the proximity element 35 of the roving probe 16 in close proximity to one of the proximity elements 25 of the mapping probe 14. As discussed, each proximity element 25 of the mapping probe 14 is preferably adjacent a mapping element 24. Therefore, during this procedure, the proximity element 35 is inherently placed in close proximity to the mapping element 24 associated with the proximity element 25.

The location determination subsystem 175 is then operated to determine an absolute location of the location element 37 of the roving probe 16 within the three-dimensional coordinate system of the volume, e.g., in a x-y-z coordinate system. Any of the embodiments of the location determination subsystem 175 discussed herein may be used to perform this determination. After the absolute location of the location element 37 is determined, this data is relayed to the location-proximity association subsystem 180.

The location-proximity association subsystem 180 is operated to calculate an absolute location of the mapping element 24 of the mapping probe 14 near which the proximity element 35 of the roving probe 16 has been placed. The location-proximity association subsystem 180 determines the absolute location of the mapping element 24 based upon the absolute location of the location element 37 and the proximity of the proximity element 25 of the mapping probe 14 to the proximity element 35 of the roving probe 16. In this case, the location-proximity association subsystem 180 will consider the proximity between the proximity elements 25 and 35 to be negligible. Assuming that any distance between the proximity element 35 and location element 37 on the roving probe 16, and any distance between the proximity element 25 and mapping element 24 on the mapping probe 14, is also negligible, the location-proximity association subsystem 180 assigns the absolute location of the location element 37 to the mapping element 24. Of course, if the proximity element 35 and location element 37, or the proximity element 25 and mapping element 24, are embodied in a single element, the distance between the two elements will be zero. Alternatively, if the distance between the proximity element 35 and location element 37 is known, the absolute location of the proximity element 35 can be determined by adjusting the absolute location of the location element 37 by the known distance, which calculation may be facilitated by calculating the orientation of the roving probe 16 from the location element 37. In this case, the absolute location of the proximity element 35 will be assigned to the mapping element 24.

The location-proximity association subsystem 180 then stores the absolute location of the above-mentioned mapping element 24 in memory 185. In one embodiment, the steps for determining the absolute location of a mapping element 24 are then repeated for each of the remaining mapping elements 24 on the mapping probe 14. The absolute locations for each of the remaining mapping elements 24 are likewise stored in memory 185 by the location-proximity association subsystem 180.

Alternatively, the location-proximity association subsystem 180 calculates the absolute locations for each of the remaining mapping elements 24 through an extrapolation process. For example, the positions of the mapping elements 24 on the mapping probe 14 are typically known values. Therefore, after the location-proximity association subsystem 180 determines the absolute location of a mapping elements 24, using the aforementioned steps, the location-proximity association subsystem 180 may determine the locations of the remaining mapping elements 24 in based upon the known distances on the mapping probe 14 between the remaining mapping elements 24 and the mapping element 24 for which an absolute location had been determined. Because the distal structure 20 of the mapping probe 14 might be oriented in any number of directions, the orientation of the distal structure 20 is preferably determined. To this end, the location-proximity association subsystem 180 determines the location of at least three mapping elements 24, and from that determines the orientation of the distal structure 20 of the mapping probe 14. In this manner, the absolute locations of the remaining mapping elements 24 in the three-dimensional coordinate system can be calculated from the absolute location of the first mapping element 24 and the determined orientation of the distal structure 20.

It should be noted that in the case where the distal structure 20 of the mapping probe 14 carries one or more location elements 37, geometric calculation of the remaining mapping elements 24 can be facilitated. For example, the orientation of the distal structure 20 can be determined by determining the orientation of one of the location elements 37, e.g., if it is a three-dimensional magnetic sensor. The orientation of the distal structure 20 can also be determined by determining the absolute locations of three properly spaced location elements 37, e.g., if they are ultrasonic transducers, and from that, geometrically calculating the orientation of the distal structure 20. Placement of location elements 37 on the distal structure 20 of the mapping probe 14 is especially useful when the distal structure 20 is subject to structural distortion in the presence of compressive forces, i.e., when the distal structure 20 is flimsy. Thus, the geometry of the distal structure 20 will be distorted, thus distorting the geometric calculations of the absolute positions of the remaining mapping elements 24 even if the orientation of the structural structure 20 is known. In this case, the absolute positions of the location elements 37 will reflect the nature of the distal structure 20 distortion. The absolute location calculations of the remaining mapping elements 24 can then be adjusted based on the known geometric distortion of the distal structure 20.

It is noted that, regardless of which method is used, the determinations of the absolute or precise locations of the mapping elements 24 may be performed several times in succession in order to generate an enhanced knowledge of the positions of the mapping elements 24 within the space. As the absolute locations of the mapping elements 24 are being stored in memory 185 the location-proximity association subsystem 180 outputs them to the display 150 for visualization by the physician. Alternatively, the absolute location of the mapping elements 24 can be displayed prior to or subsequent to their storage. In the preferred method, a wire model representation of the mapping probe 14, showing the absolute locations of each mapping element 24 within the three dimensional coordinate system, is displayed, as illustrated in FIG. 15. The display of the wire mode representation of the mapping probe 14 is preferably updated on a real-time basis. That is, the absolute locations of the mapping elements 24 are periodically determined, stored, and displayed.

After the absolute locations of the mapping elements 24 are determined, stored, and displayed, the mapping probe 14 and the mapping processing system 32 are operated to identify a target site or sites for treatment. Alternatively, the target site identification can be performed prior to determining the absolute locations of the mapping elements 24, e.g., if it is expected that the absolute locations of the mapping elements 24 will not move relative to the volume in which they are associated. In any event, to identify target sites within the volume, the mapping processing system 32 analyzes electrical activity sensed by the mapping elements 24 to identify sites on the tissue within the volume that are appropriate for treatment. As a result of this process, the mapping processing system 32 creates a cardiac activity map of the volume. It will be appreciated that other maps may be created, such as, e.g., propagation velocity maps, tissue characteristics maps, and heart wall kinetic maps. The absolute locations of the target sites within the three-dimensional coordinate system are then estimated by associating the absolute locations of the mapping elements 24 adjacent to the targeted sites to the absolute locations of the target sites themselves, or alternatively, through extrapolation based on the absolute locations of the mapping elements 24 adjacent to the targeted sites and the nature of the mapping measurements. As a result, a registered map of the three-dimensional space, in this case a registered map of cardiac activity, is created.

Regardless of how the absolute locations of the target sites are determined, the location-proximity association subsystem 180 outputs the locations of the target sites X to the display 150 for visualization by the physician. In the preferred method, the positions of the target sites X are also updated on the display 150 by adjusting the initial positions of the target sites X with any change in absolute location for each mapping element 24.

If refinement of the registered map is needed, the roving probe 16 is maneuvered within the three-dimensional space, after the registration of the mapping elements 24 and the target sites X, to add additional data points to the registered map of the three-dimensional space. With this procedure, the registered map is refined with the roving probe 16 through the addition of data points for locations not physically covered by the mapping elements 24 of the mapping probe 14. It should be noted that this map refinement process should not be limited to the specific method of initially generating the map discussed herein, but can be applied to any map that is registered in a three-dimensional system.

In one preferred method, the mapping probe 14 is left within the three-dimensional space, and the mapping element 33 of the roving probe 16 is moved between the mapping elements 24 of the mapping probe 14, within the space 22 defined by the structure 20 of the mapping probe 14, and at other locations within the volume, to gather additional data points. The roving probe 16 is placed at a location within the volume, and the absolute location of the location element 37 is determined. Using the mapping element 33 of the roving probe 16, local information regarding the location is gathered. The absolute location of the location element 37 and the local information gathered from the mapping element 33 is correlated to generate an additional data point. The additional data point is added to the initially registered map in order to render a more detailed representation of the three-dimensional space.

In another preferred method, the mapping probe 14 is removed from volume. The roving probe 16 is then maneuvered within the space 22 defined by the removed structure 20 by reference to the registered absolute locations of the mapping elements 24. Next, the absolute location of the location element 37 of the roving probe 16 at additional points within the three-dimensional space is determined. Local information regarding the additional points is gathered from the mapping element 33 and correlated with the absolute location of the location element 37 at those points to create additional data points. The registered map of the space is augmented with these data points.

Once displayed, the physician guides a therapeutic catheter to the target sites X for therapeutic delivery of, e.g., ablation energy. In the illustrated embodiment, ablation energy can be delivered by the ablation electrode 36 located on the roving probe 16. To this end, the location determination subsystem 175 is operated to determine the absolute location of the ablation element 36 on the roving probe 16 based on the absolute location of the location element 37.

Specifically, the absolute location of the location element 37 is determined, which is then adjusted by the known distance between the location element 37 and ablation electrode 36, which adjusted absolute position is then assigned to the ablation electrode 36. Of course, if the proximity element 35 and location element 37 are embodied in a single element, no adjustment is necessary.

The location-proximity association subsystem 180 then outputs the absolute location data for the ablation element 36 on the display 150, along with the absolute positions of the mapping elements 24 and the target sites X as previously discussed. Preferably, the output on the display 150 of the absolute location data for the ablation element 36 is performed substantially simultaneously with the determination of the absolute location for the ablation element 36. This is illustrated in FIG. 15. As the roving probe 16 is maneuvered within the space or volume, and toward a target site X, the location determination subsystem 175 provides real-time updated absolute position information for the ablation element 36 to the location-proximity association subsystem 180. The location-proximity association subsystem 180, in turn, updates the position of the ablation element 36 on the display 150, which in the preferred method, is displayed with the updated wire mesh model of the mapping probe 14 and target sites X.

Therefore, the system 10 is able to guide a user or physician in maneuvering an ablation element 36 to a target site X by continually displaying an updated representation of the mapping elements 24, the target sites X, and the ablation element 36, all relative to a three-dimensional coordinate system with the subject space or volume. It should be noted that to allow free movement of the roving probe 16, the mapping probe 14 is preferably removed from the volume. This is made possible by the fact that the once the volume is mapped and registered, it can be freely retrieved from memory without further use of the mapping probe 14. Alternatively, the mapping probe 14 can be left in the volume in case further mapping is needed.

Once the user or physician positions the ablation element 36 adjacent a target site X, the user or physician is then able to operate the RF ablation system 46 to deliver ablation energy to treat the site X. Alternatively, the ablation element 36 may be substituted with other treatment elements, such as, e.g., a therapeutic agent delivery element. In this case, the user delivers a therapeutic agent rather than ablation energy to the target site X. All of the other processing steps with regard to determining the absolute position of the ablation element 36 and guiding a user in maneuvering the ablation element 36 to a target site X apply equally to the determination of an absolute location of, and guiding a user in maneuvering, an alternative treatment element.

The three-dimensional space or volume within which the present invention operates may be any location within a patient's body, such as, e.g., the esophagus, a heart chamber, or any other body cavity. The three-dimensional space or volume may be comprised of more than one subvolume. As one example, when the system 10 is operated in a volume that comprises subvolumes, the mapping probe 14 and roving probe 16 are first placed within a first subvolume, such as, e.g., in the right atrium. The absolute locations of the mapping elements 24 of the mapping probe 14 within the three-dimensional coordinate system are then determined and stored, using the procedures previously described. The mapping processing system 32 is operated to identify any target sites that may be present in the first subvolume. The absolute locations of these target sites within the three-dimensional coordinate system are then determined and stored.

The mapping probe 14 and roving probe 16 are then removed from the first subvolume, and are then positioned in a second subvolume, such as, e.g., the left atrium. In the second subvolume, the absolute positions of the mapping elements 24 relative to the three-dimensional coordinate system is determined and stored, using the previously described methods. Additionally, any target sites within the second volume are identified, and their absolute positions are determined and stored in the manner described above.

In a similar manner as shown in FIG. 15, the location-proximity association subsystem 180 then outputs the absolute position data for the mapping elements 24 and target sites in the first and second subvolumes for visualization by the physician. Once displayed, the physician can then guide the ablation element 36 of the roving probe 16 to, and treat, the target sites X in each of the first and second subvolumes, in the previously described manner. It should be noted that, to minimize manipulation of the roving catheter 16 between the first and second subvolumes, treatment of the target sites X within the first subvolume can be performed prior to removal of the roving catheter 16 from the first subvolume. In addition, because the ablation procedure would be accomplished when the mapping probe 14 is still within the first subvolume, the absolute positions of the mapping elements 24 and the target sites X can be updated and displayed real-time to facilitate the ablation process.

In another preferred method, where the three-dimensional space in which the mapping probe 14 and the roving probe 16 are placed is comprised of a plurality of subvolumes, the mapping probe 14 may include a first catheter and a second catheter, each of which carries at least one mapping element 24. The first and second catheters of the mapping probe 14 are then placed in different subvolumes, e.g., the left and the right atria, or the high right atrium and the area around the tricuspid valve annulus. The roving probe 16 is then placed within the first subvolume, and the absolute locations of the mapping elements 24 on the first catheter of the mapping probe 14 within the three-dimensional coordinate system are then determined and stored, using the procedures previously described. The mapping processing system 32 is operated to identify any target sites that may be present in the first subvolume. The absolute locations of these target sites within the three-dimensional coordinate system are then determined and stored.

The roving probe 16 is then removed from the first subvolume and positioned in the second subvolume. The absolute positions of the mapping elements 24 on the second catheter of the mapping probe 14 within the three-dimensional coordinate system are then determined and stored, using the previously described methods. Additionally, any target sites within the second volume are identified, and their absolute positions are determined and stored, also in the manner described above. The location-proximity association subsystem 180 then outputs the absolute position data for the mapping elements 24 of the first and second catheters, as well as the target sites, in the first and second subvolumes for visualization by the physician.

In a similar manner as shown in FIG. 15, the location-proximity association subsystem 180 then outputs the absolute position data for the mapping elements 24 of the first and second catheters of the mapping probe 14, as well as the target sites, associated with the first and second subvolumes for visualization by the physician. Once displayed, the physician can then guide the ablation element 36 of the roving probe 16 to, and treat, the target sites X in each of the first and second subvolumes, in the previously described manner. Like with the previously described method, to minimize manipulation of the roving catheter 16 between the first and second subvolumes, treatment of the target sites X within the first subvolume can be performed prior to removal of the roving catheter 16 from the first subvolume.

It should be noted that when operating in a subject volume comprised of subvolumes (whether using one or two catheters), a composite map of the volume comprising subvolumes may be output on the display 150. That is, the data regarding the absolute positions of the mapping elements 24 and target sites within the first subvolume are presented in conjunction with similar data from the second subvolume in order to present a single composite map on the display 150. Alternatively, the location-proximity association subsystem 180 may output two discrete maps of the subvolumes, rather than a single composite map of the entire volume, on the display 150. For example, the data regarding the first subvolume may be presented side-by-side with the data regarding the second subvolume. Or, the data regarding the first subvolume and second volume may be output on two discrete displays.

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims.

What is claimed is:

1. A method of mapping a body cavity of a patient, comprising:

positioning a first probe carrying a plurality of mapping elements in the body cavity, wherein the plurality of mapping elements are located adjacent a plurality of locations along the body cavity;

positioning a second probe carrying a functional element in the body cavity; determining an absolute position of the functional element within a three-dimensional coordinate system;

determining a proximity of the functional element to each of the plurality of mapping elements;

determining an absolute position within the coordinate system of each of the plurality of mapping elements based on the absolute position of the functional element and the proximity of the functional element to each of the plurality of mapping elements;

generating a map by detecting information local to the body cavity using the plurality of mapping elements and associating the local information to the absolute positions of the plurality of mapping elements;

locating the functional element adjacent a location on the body cavity between the plurality of locations, wherein the functional element comprises a mapping element;

determining an absolute position of the mapping element within the coordinate system; and detecting information local to the body cavity using the mapping element and associating the local information to the absolute position of the mapping element to refine the map.

2. The method of claim 1, further comprising storing the refined map in memory.

3. The method of claim 2, further comprising: retrieving the refined map from memory; and displaying the refined map.

4. The method of claim 3, further comprising navigating a device in the coordinate system by reference to the displayed refined map.

5. The method of claim 4, wherein the device comprises the second probe.

6. The method of claim 4, wherein the device is a therapeutic device, and the local information comprises information indicating tissue targeted for therapy, the method further comprising treating the targeted tissue with the device.

7. The method of claim 6, wherein the therapeutic device comprises an ablation electrode, and the targeted tissue is ablated.

8. The method of claim 1, further comprising removing the first probe from the body cavity prior to locating the functional element adjacent the body cavity location.

9. The method of claim 1, further comprising maintaining the first probe within the body cavity while locating the functional element adjacent the body cavity location.

10. The method of claim 1, wherein the body cavity is a heart chamber.

11. A method of mapping a body cavity of a patient, comprising:

positioning a first probe carrying a plurality of mapping elements in the body cavity, wherein the plurality of mapping elements are located adjacent a plurality of locations along the body cavity;

positioning a second probe carrying a mapping element in the body cavity;

determining an absolute position within the coordinate system of each of the plurality of mapping elements;

generating a map by detecting information local to the body cavity using the plurality of mapping elements and associating the local information to the absolute positions of the plurality of mapping elements;

locating the mapping element adjacent a location on the body cavity between the plurality of locations;

determining an absolute position of the mapping element within the coordinate system; and detecting information local to the body cavity using the mapping element and associating the local information to the absolute position of the mapping element to refine the map.

12. The method of claim 11, further comprising storing the refined map in memory.

13. The method of claim 12, further comprising: retrieving the refined map from memory; and displaying the refined map.

14. The method of claim 13, further comprising navigating a device in the coordinate system by reference to the displayed refined map.

15. The method of claim 14, wherein the device comprises the second probe.

16. The method of claim 14, wherein the device is a therapeutic device, and the local information comprises information indicating tissue targeted for therapy, the method further comprising treating the targeted tissue with the device.

17. The method of claim 16, wherein the therapeutic device comprises an ablation electrode, and the targeted tissue is ablated.

18. The method of claim 11, further comprising removing the first probe from the body cavity prior to locating the functional element adjacent the body cavity location.

19. The method of claim 11, further comprising maintaining the first probe within the body cavity while locating the functional element adjacent the body cavity location.

20. The method of claim 11, wherein the body cavity is a heart chamber.

21. A method of mapping a body cavity of a patient, comprising:

positioning a mapping probe within the body cavity;

generating a map of the body cavity with the mapping probe;

registering the map within a three-dimensional coordinate system;

positioning a roving probe in the body cavity; and refining the map with the roving probe.

22. The method of claim 21, wherein the roving probe carries a mapping element, and the map is refined by:

locating the mapping element adjacent a location on the body cavity;

determining an absolute position of the mapping element within the coordinate system; and detecting information local to the body cavity using the mapping element and associating the local information to the absolute position of the mapping element.

23. The method of claim 21, further comprising storing the refined map in memory.

24. The method of claim 23, further comprising: retrieving the refined map from memory; and displaying the refined map.

25. The method of claim 24, further comprising navigating a device in the coordinate system by reference to the displayed refined map.

26. The method of claim 25, wherein the device comprises the roving probe.

27. The method of claim 25, wherein the device is a therapeutic device and the refined map comprises information indicating tissue targeted for therapy, the method further comprising treating the targeted tissue with the device.

28. The method of claim 27, wherein the therapeutic device comprises an ablation electrode, and the targeted tissue is ablated.

29. The method of claim 21, further comprising removing the mapping probe from the body cavity prior to completion of map refinement.

30. The method of claim 21, further comprising maintaining the mapping probe within the body cavity until completion of the map refinement.

31. The method of claim 21, wherein the body cavity is a heart chamber.

32. A system for mapping a body cavity, comprising:

a first probe having a distal portion carrying a plurality of mapping elements and one or more location elements;

a second probe having a distal portion carrying a mapping element and a location element;

a mapping processing subsystem in communication with the plurality of mapping elements and the mapping element, and being configured for generating a map by detecting information local to the body cavity using the plurality of mapping elements and the mapping element;

a location determination subsystem in communication with the one or more location elements and the location element and being configured to determine absolute positions of the plurality of mapping elements and the mapping element in a three-dimensional coordinate system based on locations of the one or more location elements and the location element; and a registration subsystem in communication with the mapping processing subsystem and the location determination subsystem, and being configured to associate the local information to the absolute positions of the plurality of mapping elements and the mapping element.

33. The system of claim 32, further comprising memory in communication with the registration subsystem for storing the refined map.

34. The system of claim 33, further comprising a display in communication with the registration subsystem for displaying the refined map.

35. The system of claim 34, further comprising a device carrying another location element, wherein the location determination subsystem is further in communication with another location element and being configured to determine an absolute position of the another location element.

36. The system of claim 35, wherein the device comprises the second probe.

37. The system of claim 35, wherein the device is a therapeutic device, and the local information comprises information indicating tissue targeted for therapy.

38. The system of claim 37, wherein the therapeutic device comprises an ablation electrode.

39. The system of claim 32, wherein the first probe comprises a 3-D catheter structure on which the plurality of mapping elements is carried.

40. The system of claim 39, wherein the 3-D catheter structure is 40 millimeters or less in size.

* * * * *